(12) United States Patent
Zhang et al.

(10) Patent No.: US 8,497,079 B2
(45) Date of Patent: Jul. 30, 2013

(54) GLUCAGON DETECTION AND QUANTITATION BY MASS SPECTROMETRY

(75) Inventors: Yanni Zhang, Mission Viejo, CA (US); Nigel J. Clarke, Oceanside, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

(21) Appl. No.: 13/517,483

(22) PCT Filed: Dec. 20, 2010

(86) PCT No.: PCT/US2010/061353
§ 371 (c)(1),
(2), (4) Date: Aug. 28, 2012

(87) PCT Pub. No.: WO2011/084751
PCT Pub. Date: Jul. 14, 2011

(65) Prior Publication Data
US 2013/0005050 A1    Jan. 3, 2013

Related U.S. Application Data

(60) Provisional application No. 61/288,785, filed on Dec. 21, 2009.

(51) Int. Cl.
*G01N 33/53* (2006.01)
*G01N 31/00* (2006.01)

(52) U.S. Cl.
USPC ........... 435/7.21; 435/7.1; 436/501; 436/518; 424/9.1; 424/520; 530/300; 530/350

(58) Field of Classification Search
None
See application file for complete search history.

(56) References Cited

U.S. PATENT DOCUMENTS

| | | | |
|---|---|---|---|
| 5,772,874 | A | 6/1998 | Quinn et al. |
| 5,795,469 | A | 8/1998 | Quinn et al. |
| 5,919,368 | A * | 7/1999 | Quinn et al. ................. 210/635 |
| 5,968,367 | A * | 10/1999 | Quinn et al. ................. 210/656 |
| 6,107,623 | A | 8/2000 | Bateman et al. |
| 6,124,137 | A * | 9/2000 | Hutchens et al. ............. 436/155 |
| 6,204,500 | B1 | 3/2001 | Whitehouse et al. |
| 6,268,144 | B1 | 7/2001 | Koster |
| 6,995,364 | B2 * | 2/2006 | Makarov et al. ............. 250/290 |
| 2006/0228809 | A1 | 10/2006 | Clarke et al. |
| 2006/0252134 | A1 | 11/2006 | Lorbert et al. |
| 2008/0118932 | A1 | 5/2008 | Toler et al. |
| 2008/0258054 | A1 | 10/2008 | Cotter |
| 2009/0048797 | A1 | 2/2009 | Tolmachev et al. |
| 2009/0090856 | A1 | 4/2009 | Grant et al. |
| 2009/0289182 | A1 | 11/2009 | Pevsner |

FOREIGN PATENT DOCUMENTS
EP    0 133 540    2/1985

OTHER PUBLICATIONS

Bartolucci, et al., "Liquid chromatography tandem mass spectrometric quantitation of sulfamethazine and its metabolites: direct analysis of swine urine by triple quadrupole and by ion trap mass spectrometry", Rapid Communications in Mass Spectrometry (2000), 14:967-973.
Bredehöft, et al., "Quantification of human insulin-like growth factor-1 and qualitative detection of its analogues in plasma using liquid chromatography/electrospray ionization tandem mass spectrometry", Rapid Commun. Mass Spectrom., (2008) 22:477-485.
Delinsky, et al., "Quantitation of the large ploypeptide glucagon by protein precipitation and LC/MS", Biomedical Chromatography, (2004), 18; 700-705.
Ichiba, et al., "Analysis of hydroxyl radical-induced oxidation process of glucagon by reversed-phase HPLC and ESI-MS/MS", Biomedical Chromatography, 2009, 23, 1051-1058.
International Preliminary Report on Patentability issued for PCT/US2010/061353 on Jul. 5, 2012.
International Search Report issued for PCT/US2010/061353 on Mar. 1, 2011.
Le Breton, et al., "Direct determination of recombinant bovine somatotropin in plasma from a treated goat by liquid chromatography/high-resolution mass spectrometry", Rapid Communication Mass Spectrometry (2008) 22:3130-3136.
Matilainen, et al., "The stability and dissolution properties of solid glucagon/γ-cyclodextrin powder", European Journal of Pharmaceutical Sciences, 36, 2009, 412-420.
Merchant et al., "Recent advancements in surface-enhanced laser desorption/ionization-time of flight-mass spectrometry", Electrophoresis (2000), 21: 1164-1177.
Olsen, et al., "Higher-energy C-trap dissociation for peptide modification analysis", Nature Methods, (2007) vol. 4, No. 9:709-712.
Poison, et al., "Optimization of protein precipitation based upon effectiveness of protein removal and ionization effect in liquid chromatography-tandem mass spectrometry" Journal of Chromatography B (2003), 785:263-275.
Robb, et al., "Atmospheric pressure photoionization: An ionization method for liquid chromatography-mass spectrometry", Analytical Chemistry (2000) 72(15): 3653-3659.
Rogatsky, et al., "Trace LC/MS quantitative analysis of polypeptide biomarkers: Impact of 1-D and 2-D chromatography on matrix effects and sensitivity" J. Sep. Sci., 2007, 30, 226-233.
Schenk, et al., "A high confidence, manually validated human blood plasma protein reference set", BMC Medical Geonomics (2008) 1:41: 28 pages.

(Continued)

*Primary Examiner* — Lisa Cook
(74) *Attorney, Agent, or Firm* — Foley & Lardner LLP

(57) ABSTRACT

Methods are described for measuring the amount of glucagon in a sample. More specifically, mass spectrometric methods are described for detecting and quantifying glucagon in a sample.

30 Claims, 14 Drawing Sheets

OTHER PUBLICATIONS

Silvertand, et al., "Development and characterization of cIEF-MALDI-TOF MS for protein analysis", Electrophoresis, 2009, 30, 1828-1835.

Thevis, et al., "Mass spectrometric determination of insulins and their degradation products in sports drug testing", Mass Spectrometry Reviews (2008) 27:35-50.

Thomas, et al., "Mass spectrometric determination of gonadotrophin-releasing hormone (GnRH) in human urine for doping control purposes by means of LC-ESI-MS/MS", Journal of Mass Spectrometry (2008) 43:908-915.

Wright, et al. "Proteinchip ® surface enhanced laser desorption/ionization (SELDI) mass spectrometry: a novel protein biochip technology for detection of prostate cancer biomarkers in complex protein mixtures", Prostate Cancer and Prostatic Diseases (1999) 2: 264-276.

Zimmer, et al. "Comparison of turbulent-flow chromatography with automated solid-phase extraction in 96-well plates and liquid-liquid extraction used as plasma sample preparation techniques for liquid chromatography-tandem mass spectrometry", Journal of Chromatography A, (1999).854: 23-35.

* cited by examiner

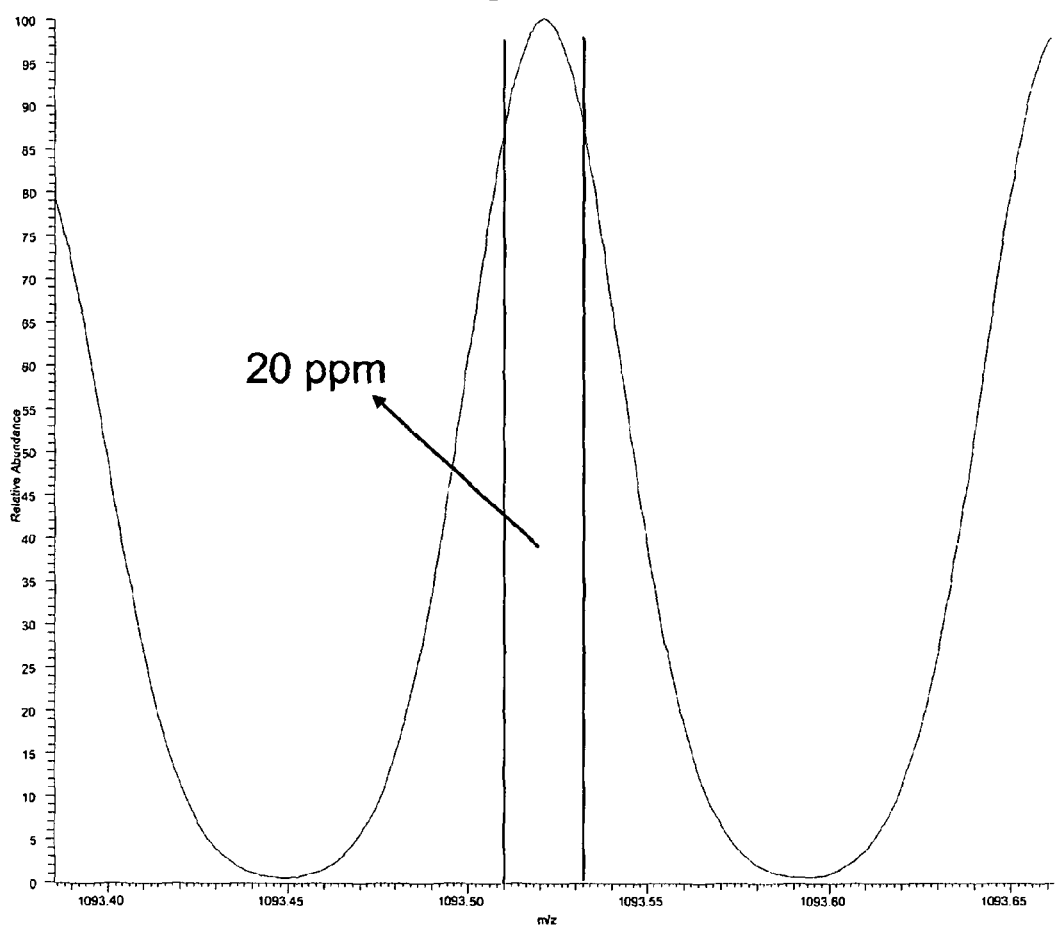

GLUCAGON DETECTION AND QUANTITATION BY MASS SPECTROMETRY

CROSS-REFERENCE TO RELATED APPLICATIONS

This application is a U.S. National Stage of PCT/US2010/061353, filed Dec. 20, 2010, which claims priority to U.S. Provisional Application No. 61/288,785, filed Dec. 21, 2009. The entire contents of the foregoing applications are hereby incorporated by reference in their entirety.

FIELD OF THE INVENTION

The invention relates to the detection and quantitation of glucagon. In particular, the invention relates to methods for detection and quantitation of glucagon by mass spectrometry.

BACKGROUND OF THE INVENTION

The following description of the background of the invention is provided simply as an aid in understanding the invention and is not admitted to describe or constitute prior art to the invention.

Glucagon is an important hormone involved in carbohydrate metabolism. Glucagon is normally secreted by $\alpha_2$-cells in the pancreas when blood glucose levels start to fall too low, causing the liver to convert stored glycogen into glucose and release it into the bloodstream, raising blood glucose levels and ultimately preventing the development of hypoglycemia. Thus, glucagon exerts a counterbalancing effect to insulin in the regulation of glucose metabolism.

The biologically active form of glucagon consists of 29 amino acids with a molecular weight of about 3482.8 Da. A much larger form (about 160 kDa) may represent binding of the ~3500 Da glucagon to plasma protein. In rare cases, individuals may have increased amounts of this larger form in circulation.

Glucagon may be down regulated in diabetes mellitus (occasional) and hypoglycemia patients. Glucagon may be up regulated in newborns, glucagonoma, and diabetes mellitus (relative or actual) patients. Glucagonoma may present as three different syndromes. The first consists of a characteristic skin rash, necrolytic migratory erythema, diabetes mellitus or impaired glucose tolerance, weight loss, anemia, and veneous thrombosis. This form usually shows very high glucagon levels, such as greater than 1000 pg/mL. The second is associated with severe diabetes. The third is associated multiple endocrine neoplasia syndrome. This form may have relatively lower glucagon levels.

Various mass spectrometric methods have been reported for detecting and/or quantitating glucagon. See, e.g., Delinsky, D., et al., *Biomed. Chromatogr.* 2004, 18:700-5 (reporting quantitation of glucagon with LC-MS (ion trap)); Rogatsky, E., et al., *J. Sep. Sci.* 2007, 30:226-33 (reporting that LC-MS is preferred to LC-MS/MS for glucagon); Matilainen, L., et al., *Eur. J. Pharm. Sci.* 2009, 36:412-20 (reporting quantitation of glucagon in solid state samples by HPLC-MS (ion trap)); Silvertand, L., et al., *Electrophoresis* 2009, 30:1828-35 (reporting MALDI-TOF MS detection of glucagon and its deamidation product); Ichiba, H., et al., *Biomed. Chromatogr.* 2000, 23:1051-58 (reporting ion trap MS of glucagon and ion trap $MS^2$ of oxidized glucagon).

SUMMARY OF THE INVENTION

The present invention provides methods for detecting the presence or amount of glucagon in a sample by mass spectrometry. The methods include subjecting the sample to ionization under conditions suitable to produce one or more ions detectable by mass spectrometry; determining the amount of one or more ions by mass spectrometry; and using the amount of one or more ions to determine the amount of glucagon in the sample.

In some embodiments, mass spectrometry comprises tandem mass spectrometry. In these embodiments, the methods include: a) ionizing the sample under conditions suitable to produce a glucagon precursor ion; b) fragmenting a glucagon precursor ion to produce one or more fragment ions; c) determining the amount of one or more ions produced in steps a) and b); and d) using the amount of the one or more ions determined in step c) to determine the amount of glucagon in the sample. In some embodiments, a glucagon precursor ion with a mass to charge ratio (m/z) of 871.1±0.50 is fragmented to produce one or more fragment ions. In some related embodiments, one or more of the fragment ions are selected from the group consisting of ions with m/z of 780.6±0.50, 841.8±0.50, 940.8±0.50, 1002.5±0.50, 1040.2±0.50, 1083.9±0.50, and 1122.2±0.50. In some related embodiments, one or more of the fragment ions are selected from the group consisting of ions with m/z of 1040.2±0.50 and 1083.9±0.50. In some embodiments, the tandem mass spectrometry is not high definition/high accuracy mass spectrometry.

In some embodiments, mass spectrometry comprises high resolution/high accuracy mass spectrometry. In embodiments employing high resolution/high accuracy mass spectrometry, the methods include: a) subjecting the sample to ionization under conditions suitable to produce one or more ions detectable by mass spectrometry; b) determining the amount of one or more of said ions by high resolution/high accuracy mass spectrometry; and c) using the amount of the one or more ions determined in step b) to determine the amount of glucagon in the sample. In these embodiments, high resolution/high accuracy mass spectrometry is conducted with a mass analyzer capable of a FWHM of greater than or equal to about 10,000 and an accuracy of less than or equal to about 50 ppm; such as a FWHM of greater than or equal to about 20,000 and an accuracy of less than or equal to about 10 ppm; such as a FWHM of greater than or equal to about 20,000 and an accuracy of less than or equal to about 5 ppm. In these embodiments, one or more of the ions determined in step b) are selected from the group consisting of ions with mass to charge ratios of 780.6±0.50, 841.8±0.50, 871.1±0.50, 940.8±0.50, 1002.5±0.50, 1040.2±0.50, 1083.9±0.50, and 1122.2±0.50. In these embodiments, high resolution/high accuracy mass spectrometry may be conducted with any suitable mass spectrometer, such as an orbitrap mass spectrometer or a time of flight (TOF) mass spectrometer.

In embodiments utilizing tandem mass spectrometry, tandem mass spectrometry may be conducted by any method known in the art, including for example, multiple reaction monitoring, precursor ion scanning, or product ion scanning.

In embodiments utilizing high resolution/high accuracy mass spectrometry, the identity and/or amount of an ion may be determined by collecting spectrometric data from one or more peaks with each peak resulting from an isotopic form of the ion. For example, identification of a glucagon ion may be confirmed with spectrometric data from two or more isotopic peaks from the same ion. For quantitation, spectrometric data from a single peak, resulting from a single isotopic form of an ion, may be used to determine the amount of glucagon in the sample; alternatively, spectrometric data from multiple peaks, each resulting from a different isotopic form of an ion, may be used to determine the amount of glucagon in the sample.

The methods described herein may be capable of detecting glucagon at levels within the range of 60 pg/mL to 500 pg/mL, inclusive; such as within the range of 60 pg/mL to 250 pg/mL, inclusive; such as about 100 pg/mL.

In some embodiments, the sample is subjected to an extraction column, such as a solid phase extraction (SPE) column, prior to ionization. In some related embodiments, SPE and mass spectrometry are conducted with on-line processing.

In some embodiments, the sample is subjected to an analytical column, such as a high performance liquid chromatography (HPLC) column, prior to ionization. In some related embodiments, HPLC and mass spectrometry are conducted with on-line processing.

In some embodiments, the sample is subject to immunopurification prior to ionization. In some embodiments, immunopurification comprises capture and extraction of glucagon in said sample with anti-glucagon antibodies. In some embodiments, immunopurification comprises subjecting the sample to an immunoaffinity column.

In embodiments which utilize two or more of an immunoaffinity column, an extraction column, an analytical column, and an ionization source, two or more of these components may be connected in an on-line fashion to allow for automated sample processing and analysis.

In some embodiments, the sample comprises a biological sample; such as plasma or serum.

In certain preferred embodiments of the methods disclosed herein, mass spectrometry is performed in positive ion mode. Alternatively, mass spectrometry is performed in negative ion mode. Various ionization sources, including for example atmospheric pressure chemical ionization (APCI) or electrospray ionization (ESI), may be used in embodiments of the present invention. In certain embodiments, glucagon is measured using ESI in positive ion mode.

In preferred embodiments, a separately detectable internal standard is provided in the sample, the amount of which is also determined in the sample. In these embodiments, all or a portion of both the analyte of interest and the internal standard present in the sample is ionized to produce a plurality of ions detectable in a mass spectrometer, and one or more ions produced from each are detected by mass spectrometry. In these embodiments, the presence or amount of ions generated from the analyte of interest may be related to the presence of amount of analyte of interest in the sample.

In other embodiments, the amount of the glucagon in a sample may be determined by comparison to one or more external reference standards. Exemplary external reference standards include blank plasma or serum spiked with glucagon or an isotopically labeled variant thereof.

In certain embodiments, the limit of quantitation (LOQ) of glucagon is within the range of 200 pg/mL to 750 pg/mL, inclusive; preferably within the range of 200 pg/mL to 500 pg/mL, inclusive; preferably about 200 pg/mL.

As used herein, unless otherwise stated, the singular forms "a," "an," and "the" include plural reference. Thus, for example, a reference to "a protein" includes a plurality of protein molecules.

As used herein, the term "purification" or "purifying" does not refer to removing all materials from the sample other than the analyte(s) of interest. Instead, purification refers to a procedure that enriches the amount of one or more analytes of interest relative to other components in the sample that may interfere with detection of the analyte of interest. Purification of the sample by various means may allow relative reduction of one or more interfering substances, e.g., one or more substances that may or may not interfere with the detection of selected parent or daughter ions by mass spectrometry. Relative reduction as this term is used does not require that any substance, present with the analyte of interest in the material to be purified, is entirely removed by purification.

As used herein, the term "immunopurification" or "immunopurify" refers to a purification procedure that utilizes antibodies, including polyclonal or monoclonal antibodies, to enrich the one or more analytes of interest. Immunopurification can be performed using any of the immunopurification methods well known in the art. Often the immunopurification procedure utilizes antibodies bound, conjugated or otherwise attached to a solid support, for example a column, well, tube, gel, capsule, particle or the like. Immunopurification as used herein includes without limitation procedures often referred to in the art as immunoprecipitation, as well as procedures often referred to in the art as affinity chromatography.

As used herein, the term "immunoparticle" refers to a capsule, bead, gel particle or the like that has antibodies bound, conjugated or otherwise attached to its surface (either on and/or in the particle). In certain embodiments utilizing immunopurification, immunoparticles comprise sepharose or agarose beads. In alternative embodiments utilizing immunopurification, immunoparticles comprise glass, plastic or silica beads, or silica gel.

As used herein, the term "anti-glucagon antibody" refers to any polyclonal or monoclonal antibody that has an affinity for glucagon. In various embodiments the specificity of glucagon antibodies to chemical species other than glucagon may vary; for example in certain embodiments the anti-glucagon antibodies are specific for glucagon and thus have little or no affinity for chemical species other than glucagon, whereas in other embodiments the anti-glucagon antibodies are non-specific and thus bind glucagon as well as certain other chemical species.

As used herein, the term "sample" refers to any sample that may contain an analyte of interest. As used herein, the term "body fluid" means any fluid that can be isolated from the body of an individual. For example, "body fluid" may include blood, plasma, serum, bile, saliva, urine, tears, perspiration, and the like. In some embodiments, the sample comprises a body fluid sample; preferably plasma or serum.

As used herein, the term "solid phase extraction" or "SPE" refers to a process in which a chemical mixture is separated into components as a result of an affinity of components dissolved or suspended in a solution (i.e., mobile phase) for a solid through or around which the solution is passed (i.e., solid phase). SPE, as used herein, is distinct from immunopurification in that the affinity of components in the mobile phase to the solid phase is the result of a chemical or physical interaction, rather than an immunoaffinity. In some instances, as the mobile phase passes through or around the solid phase, undesired components of the mobile phase may be retained by the solid phase resulting in a purification of the analyte in the mobile phase. In other instances, the analyte may be retained by the solid phase, allowing undesired components of the mobile phase to pass through or around the solid phase. In these instances, a second mobile phase is then used to elute the retained analyte off of the solid phase for further processing or analysis. SPE, including TFLC, may operate via a unitary or mixed mode mechanism. Mixed mode mechanisms utilize ion exchange and hydrophobic retention in the same column; for example, the solid phase of a mixed-mode SPE column may exhibit strong anion exchange and hydrophobic retention; or may exhibit column exhibit strong cation exchange and hydrophobic retention.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography).

As used herein, the term "high performance liquid chromatography" or "HPLC" (sometimes known as "high pressure liquid chromatography") refers to liquid chromatography in which the degree of separation is increased by forcing the mobile phase under pressure through a stationary phase, typically a densely packed column.

As used herein, the term "turbulent flow liquid chromatography" or "TFLC" (sometimes known as high turbulence liquid chromatography or high throughput liquid chromatography) refers to a form of chromatography that utilizes turbulent flow of the material being assayed through the column packing as the basis for performing the separation. TFLC has been applied in the preparation of samples containing two unnamed drugs prior to analysis by mass spectrometry. See, e.g., Zimmer et al., *J. Chromatogr A* 854: 23-35 (1999); see also, U.S. Pat. Nos. 5,968,367, 5,919,368, 5,795,469, and 5,772,874, which further explain TFLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*, Jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 50 µm. As used in this context, the term "about" means±10%.

As used herein, the term "analytical column" refers to a chromatography column having sufficient chromatographic plates to effect a separation of materials in a sample that elute from the column sufficient to allow a determination of the presence or amount of an analyte. Such columns are often distinguished from "extraction columns", which have the general purpose of separating or extracting retained material from non-retained materials in order to obtain a purified sample for further analysis. As used in this context, the term "about" means±10%. In a preferred embodiment the analytical column contains particles of about 5 µm in diameter.

As used herein, the terms "on-line" and "inline", for example as used in "on-line automated fashion" or "on-line extraction" refers to a procedure performed without the need for operator intervention. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (I) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z"). See, e.g., U.S. Pat. Nos. 6,204,500, entitled "Mass Spectrometry From Surfaces;" 6,107,623, entitled "Methods and Apparatus for Tandem Mass Spectrometry;" 6,268,144, entitled "DNA Diagnostics Based On Mass Spectrometry;" 6,124,137, entitled "Surface-Enhanced Photolabile Attachment And Release For Desorption And Detection Of Analytes;" Wright et al., *Prostate Cancer and Prostatic Diseases* 1999, 2: 264-76; and Merchant and Weinberger, *Electrophoresis* 2000, 21: 1164-67.

As used herein, "high resolution/high accuracy mass spectrometry" refers to mass spectrometry conducted with a mass analyzer capable of measuring m/z of a charged species with sufficient precision and accuracy to confirm a unique chemical ion. Confirmation of a unique chemical ion is possible for an ion when individual isotopic peaks from that ion are readily discernable. The particular resolving power and mass accuracy necessary to confirm a unique chemical ion varies with the mass and charge state of the ion.

As used herein, the term "resolving power" or "resolving power (FWHM)" (also known in the art as "m/$\Delta m_{50\%}$") refers to an observed m/z divided by the width of the mass peak at 50% maximum height (Full Width Half Maximum, "FWHM"). The effect of differences in resolving power is illustrated in FIGS. 1A-C, which show theoretical mass spectra of a generic ion with a m/z of about 1093. FIG. 1A shows a theoretical mass spectrum from a mass analyzer with resolving power of about 3000 (a typical operating condition for a conventional quadrupole mass analyzer). As seen in FIG. 1A, no individual isotopic peaks are discernable. By comparison, FIG. 1B shows a theoretical mass spectrum from a mass analyzer with resolving power of about 10,000, with clearly discernable individual isotopic peaks. FIG. 1C shows a theoretical mass spectrum from a mass analyzer with resolving power of about 12,000. At this highest resolving power, the individual isotopic peaks contain less than 1% contribution from baseline.

As used herein a "unique chemical ion" with respect to mass spectrometry refers a single ion with a single atomic makeup. The single ion may be singly or multiply charged.

As used herein, the term "accuracy" (or "mass accuracy") with respect to mass spectrometry refers to potential deviation of the instrument response from the true m/z of the ion investigated. Accuracy is typically expressed in parts per million (ppm). The effect of differences in mass accuracy is illustrated in FIGS. 2A-D, which show the boundaries of potential differences between a detected m/z and the actual m/z for a theoretical peak at m/z of 1093.52094. FIG. 2A shows the potential range of detected m/z at an accuracy of 120 ppm. By contrast, FIG. 2B shows the potential range of detected m/z at an accuracy of 50 ppm. FIGS. 2C and 2D show the even narrower potential ranges of detected m/z at accuracies of 20 ppm and 10 ppm.

High resolution/high accuracy mass spectrometry methods of the present invention may be conducted on instruments capable of performing mass analysis with FWHM of greater than 10,000, 15,000, 20,000, 25,000, 50,000, 100,000, or even more. Likewise, methods of the present invention may be conducted on instruments capable of performing mass analysis with accuracy of less than 50 ppm, 20 ppm, 15 ppm, 10 ppm, 5 ppm, 3 ppm, or even less. Instruments capable of these performance characteristics may incorporate certain orbitrap mass analyzers, time-of-flight ("TOF") mass analyzers, or Fourier-transform ion cyclotron resonance mass analyzers. In preferred embodiments, the methods are carried out with an instrument which includes an orbitrap mass analyzer or a TOF mass analyzer.

The term "orbitrap" describes an ion trap consisting of an outer barrel-like electrode and a coaxial inner electrode. Ions are injected tangentially into the electric field between the electrodes and trapped because electrostatic interactions between the ions and electrodes are balanced by centrifugal forces as the ions orbit the coaxial inner electrode. As an ion orbits the coaxial inner electrode, the orbital path of a trapped ion oscillates along the axis of the central electrode at a harmonic frequency relative to the mass to charge ratio of the ion. Detection of the orbital oscillation frequency allows the orbitrap to be used as a mass analyzer with high accuracy (as low as 1-2 ppm) and high resolving power (FWHM) (up to about 200,000). A mass analyzer based on an orbitrap is described in detail in U.S. Pat. No. 6,995,364, incorporated by reference herein in its entirety. Use of orbitrap analyzers has been reported for qualitative and quantitative analyses of various analytes. See, e.g., U.S. Patent Application Pub. No. 2008/0118932 (filed Nov. 9, 2007); Bredehoft, et al., Rapid Commun. Mass Spectrom., 2008, 22:477-485; Le Breton, et al., Rapid Commun. Mass Spectrom., 2008, 22:3130-36; Thevis, et al., Mass Spectrom. Reviews, 2008, 27:35-50; Thomas, et al., J. Mass Spectrom., 2008, 43:908-15; Schenk, et al., BMC Medical Genomics, 2008, 1:41; and Olsen, et al., Nature Methods, 2007, 4:709-12.

As used herein, the term "operating in negative ion mode" refers to those mass spectrometry methods where negative ions are generated and detected. The term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photoionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photoionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the photoionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. See, e.g., Robb et al., *Anal. Chem.* 2000, 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase. Laser desorption thermal desorption is a technique wherein a sample containing the analyte is thermally desorbed into the gas phase by a laser pulse. The laser hits the back of a specially made 96-well plate with a metal base. The laser pulse heats the base and the heat causes the sample to transfer into the gas phase. The gas phase sample is then drawn into the mass spectrometer.

As used herein, the term "selective ion monitoring" is a detection mode for a mass spectrometric instrument in which only ions within a relatively narrow mass range, typically about one mass unit, are detected.

As used herein, "multiple reaction mode," sometimes known as "selected reaction monitoring," is a detection mode for a mass spectrometric instrument in which a precursor ion and one or more fragment ions are selectively detected.

As used herein, the term "lower limit of quantification", "lower limit of quantitation" or "LLOQ" refers to the point where measurements become quantitatively meaningful. The analyte response at this LOQ is identifiable, discrete and reproducible with a relative standard deviation (RSD %) of less than 20% and an accuracy of 85% to 115%.

As used herein, the term "limit of detection" or "LOD" is the point at which the measured value is larger than the uncertainty associated with it. The LOD is the point at which a value is beyond the uncertainty associated with its measurement and is defined as three times the RSD of the mean at the zero concentration.

As used herein, an "amount" of an analyte in a body fluid sample refers generally to an absolute value reflecting the mass of the analyte detectable in volume of sample. However, an amount also contemplates a relative amount in comparison to another analyte amount. For example, an amount of an analyte in a sample can be an amount which is greater than a control or normal level of the analyte normally present in the sample.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.50 atomic mass unit.

The summary of the invention described above is non-limiting and other features and advantages of the invention will be apparent from the following detailed description of the invention, and from the claims.

BRIEF DESCRIPTION OF THE DRAWINGS

FIGS. 2A-D show potential deviation of instrument response from the true m/z of the ion investigated for a theoretical peak at m/z of 1093.52094 at a mass accuracy of 120 ppm (FIG. 2A), a mass accuracy of 50 ppm (FIG. 2B), a mass accuracy of 20 ppm (FIG. 2C), and at a mass accuracy of 10 ppm (FIG. 2D).

DETAILED DESCRIPTION OF THE INVENTION

Figure 1A:
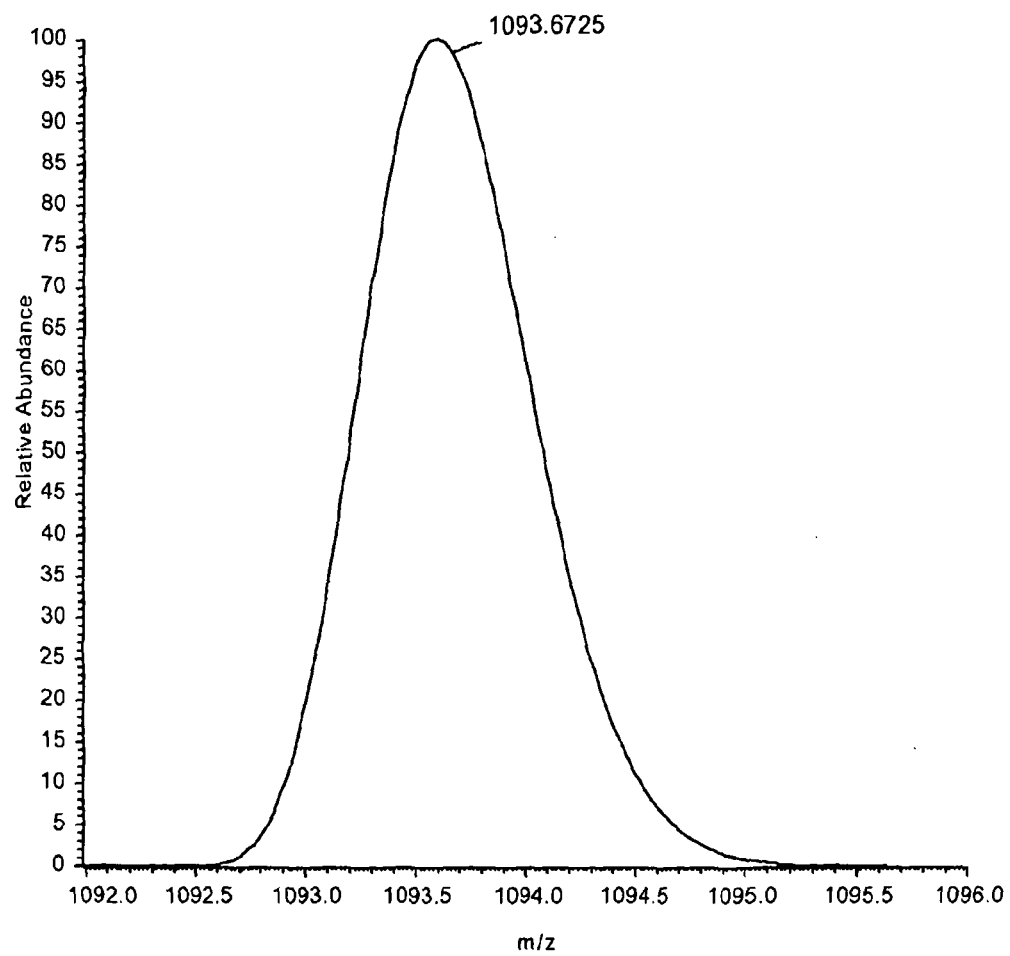
FIGS. 1A-C show theoretical mass spectra of a generic ion with a m/z of about 1093 as analyzed by a mass analyzer with resolving power of about 3000 (FIG. 1A), about 10,000 (FIG. 1B), and about 12,000 (FIG. 1C).

Methods are described for measuring the amount of glucagon in a sample. More specifically, mass spectrometric methods are described for detecting and/or quantifying glucagon in a sample. The methods may utilize solid phase extraction (SPE) and/or liquid chromatography (LC), to perform a purification of selected analytes, combined with methods of mass spectrometry (MS), thereby providing a high-throughput assay system for detecting and quantifying glucagon in a sample. As such, certain embodiments are particularly well suited for application in large clinical laboratories for an automated glucagon quantification assay.

Suitable test samples for use in methods of the present invention include any test sample that may contain the analyte of interest. In some preferred embodiments, a sample is a biological sample; that is, a sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably male or female humans. Preferred samples comprise bodily fluids such as blood, plasma, serum, saliva, cerebrospinal fluid, or tissue samples; preferably plasma and serum. Such samples may be obtained, for example, from a patient; that is, a living person, male or female, presenting oneself in a clinical setting for diagnosis, prognosis, or treatment of a disease or condition. In embodiments where the sample comprises a biological sample, the methods may be used to determine the amount of glucagon in the sample when the sample was obtained from the biological source (i.e., the amount of endogenous glucagon in the sample).

The present invention also contemplates kits for a glucagon quantitation assay. A kit for a glucagon quantitation assay may include a kit comprising the compositions provided herein. For example, a kit may include packaging material and measured amounts of an isotopically labeled internal standard, in amounts sufficient for at least one assay. Typically, the kits will also include instructions recorded in a tangible form (e.g., contained on paper or an electronic medium) for using the packaged reagents for use in a glucagon quantitation assay.

Calibration and QC pools for use in embodiments of the present invention are preferably prepared using a matrix similar to the intended sample matrix, provided that glucagon is essentially absent.

Sample Preparation for Mass Spectrometric Analysis

Typically, test samples are acidified prior to analysis. Internal standard may be added to the test samples before or after acidification.

In preparation for mass spectrometric analysis, glucagon may be enriched relative to one or more other components in the sample (e.g. protein) by various methods known in the art, including for example, liquid chromatography, filtration, centrifugation, thin layer chromatography (TLC), electrophoresis including capillary electrophoresis, affinity separations including immunoaffinity separations, extraction methods including ethyl acetate or methanol extraction, and the use of chaotropic agents or any combination of the above or the like.

Protein precipitation is one method of preparing a test sample, especially a biological test sample, such as serum or plasma. Protein purification methods are well known in the art, for example, Poison et al., *Journal of Chromatography B* 2003, 785:263-275, describes protein precipitation techniques suitable for use in methods of the present invention. Protein precipitation may be used to remove most of the protein from the sample leaving glucagon in the supernatant. The samples may be centrifuged to separate the liquid supernatant from the precipitated proteins; alternatively the samples may be filtered to remove precipitated proteins. The resultant supernatant or filtrate may then be applied directly to mass spectrometry analysis; or alternatively to liquid chromatography and subsequent mass spectrometry analysis. In certain embodiments, the use of protein precipitation such as for example, formic acid protein precipitation, may obviate the need for TFLC or other on-line extraction prior to mass spectrometry or high performance liquid chromatography (HPLC) and mass spectrometry.

Another method of sample purification that may be used prior to mass spectrometry is liquid chromatography (LC). Certain methods of liquid chromatography, including high performance liquid chromatography (HPLC), rely on relatively slow, laminar flow technology. Traditional HPLC analysis relies on column packing in which laminar flow of the sample through the column is the basis for separation of the analyte of interest from the sample. The skilled artisan will understand that separation in such columns is a partition process and may select LC, including HPLC, instruments and columns that are suitable for use with glucagon. The chromatographic column typically includes a medium (i.e., a packing material) to facilitate separation of chemical moieties (i.e., fractionation). The medium may include minute particles. The particles typically include a bonded surface that interacts with the various chemical moieties to facilitate separation of the chemical moieties. One suitable bonded surface is a hydrophobic bonded surface such as an alkyl bonded or a cyano bonded surface. Alkyl bonded surfaces may include C-4, C-8, C-12, or C-18 bonded alkyl groups. In preferred embodiments, the column is a C-8 column. The chromatographic column includes an inlet port for receiving a sample and an outlet port for discharging an effluent that includes the fractionated sample. The sample may be supplied to the inlet port directly, or from a SPE column, such as an on-line extraction column or a TFLC column. In some embodiments, an on-line filter may be used ahead of the SPE column and or HPLC column to remove particulates and phospholipids in the samples prior to the samples reaching the SPE and/or HPLC columns. In preferred embodiments, a 0.2 µm or 0.45 µm micro-spin cellulose acetate delipidation filter is used as such an off-line filter.

In one embodiment, the sample may be applied to the LC column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytypic (i.e. mixed) mode. During chromatography, the separation of materials is effected by variables such as choice of eluent (also known as a "mobile phase"), elution mode, gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In one preferred embodiment, HPLC is conducted with a polar embedded analytical column chromatographic system. In certain preferred embodiments, a polar embedded C-8 analytical column (e.g., a LUNA C8(2) analytical column from Phenomenex Inc. (5 µm particle size, 20×2.1 mm), or equivalent) is used. In certain preferred embodiments, HPLC is performed using HPLC Grade 0.2% aqueous formic acid as solvent A, and 0.1% formic acid in acetonitrile as solvent B.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In some embodiments, TFLC may be used for purification of glucagon prior to mass spectrometry. In such embodiments, samples may be extracted using a TFLC column which captures the analyte. The analyte is then eluted and transferred on-line to an analytical HPLC column. For example, sample extraction may be accomplished with a TFLC extraction cartridge may be accomplished with a large particle size (50 µm) packed column. Sample eluted off of this column is then transferred on-line to an HPLC analytical column for further purification prior to mass spectrometry. Because the steps involved in these chromatography procedures may be linked in an automated fashion, the requirement for operator involvement during the purification of the analyte can be minimized. This feature may result in savings of time and costs, and eliminate the opportunity for operator error.

In some embodiments, the methods include immunopurifying glucagon prior to mass spectrometry analysis. The immunopurification step may be performed using any of the immunopurification methods well known in the art. Often the immunopurification procedure utilizes antibodies bound, conjugated, immobilized or otherwise attached to a solid support, for example a column, well, tube, capsule, particle or the like. Generally, immunopurification methods involve (1) incubating a sample containing the analyte of interest with antibodies such that the analyte binds to the antibodies, (2) performing one or more washing steps, and (3) eluting the analyte from the antibodies.

In certain embodiments the incubation step of the immunopurification is performed with the antibodies free in solution and the antibodies are subsequently bound or attached to a solid surface prior to the washing steps. In certain embodiments this can be achieved using a primary antibody that is an anti-glucagon antibody and a secondary antibody attached to a solid surface that has an affinity to the primary anti-glucagon antibody. In alternative embodiments, the primary antibody is bound to the solid surface prior to the incubation step.

Appropriate solid supports include without limitation tubes, slides, columns, beads, capsules, particles, gels, and the like. In some preferred embodiments, the solid support is a multi-well plate, such as, for example, a 96 well plate, a 384-well plate or the like. In certain preferred embodiments the solid support are sepharose or agarose beads or gels. There are numerous methods well known in the art by which antibodies (for example, an anti-glucagon antibody or a secondary antibody) may be bound, attached, immobilized or coupled to a solid support, e.g., covalent or non-covalent linkages adsorption, affinity binding, ionic linkages and the like. In some embodiments antibodies are coupled using CNBr, for example the antibodies may be coupled to CNBr activated sepharose. In other embodiments, the antibody is attached to the solid support through an antibody binding protein such as protein A, protein G, protein A/G, or protein L.

The washing step of the immunopurification methods generally involve washing the solid support such that the glucagon remain bound to the anti-glucagon antibodies on the solid support. The elution step of the immunopurification generally involves the addition of a solution that disrupts the binding of glucagon to the anti-glucagon antibodies. Exemplary elution solutions include organic solutions (preferably ethanol), salt solutions, and high or low pH solutions.

In certain preferred embodiments, immunopurification is performed using immunoparticles having anti-glucagon antibodies. In certain preferred embodiments the test sample possibly containing glucagon and the immunoparticles are mixed in a tube for incubation and binding of glucagon to the anti-glucagon antibodies attached to the immunoparticles; the tube is centrifuged leaving the immunoparticles in a pellet; the supernatant is removed; the immunoparticles are washed one or more times by adding a solution to the pellet and recentrifuging; and the glucagon are eluted by adding an elution solution to the immunoparticles, the tube is centrifuged leaving the immunoparticles in a pellet; and the supernatant containing glucagon is collected. In related preferred embodiments, the immunopurification is performed using a column or cartridge that contains immunoparticles having anti-glucagon antibodies. Preferably, the such column or cartridge is configured and arranged in a manner to allow solutions to flow through while keeping the immunoparticles contained therein. In certain preferred embodiments, the solution is forced through the column or cartridge by gravity, centrifugation or pressure. The use of columns may improve the ease of performing the incubation, washing and elution steps. In some embodiments, the immunopurification may be performed by affinity chromatography; such as automated affinity chromatography.

Detection and Quantitation by Mass Spectrometry

In various embodiments, glucagon may be ionized by any method known to the skilled artisan. Mass spectrometry is performed using a mass spectrometer, which includes an ion source for ionizing the fractionated sample and creating charged molecules for further analysis. For example ionization of the sample may be performed by electron ionization, chemical ionization, electrospray ionization (ESI), photon ionization, atmospheric pressure chemical ionization (APCI), photoionization, atmospheric pressure photoionization (APPI), Laser diode thermal desorption (LDTD), fast atom bombardment (FAB), liquid secondary ionization (LSD, matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

Glucagon may be ionized in positive or negative mode. In some embodiments, glucagon is ionized by ESI in positive mode.

In mass spectrometry techniques generally, after the sample has been ionized, the positively or negatively charged ions thereby created may be analyzed to determine a mass to charge ratio (m/z). Suitable analyzers for determining m/z include quadrupole analyzers, ion traps analyzers, and time-of-flight analyzers. Exemplary ion trap methods are described in Bartolucci, et al., *Rapid Commun. Mass Spectrom.* 2000, 14:967-73.

According to some methods of the present invention, high resolution/high accuracy mass spectrometry is used for quantitation of glucagon. That is, mass spectrometry is conducted with a mass spectrometer capable of exhibiting a resolving power (FWHM) of at least 10,000, with accuracy of about 50 ppm or less for the ions of interest; preferably the mass spectrometer exhibits a resolving power (FWHM) of 20,000 or better and accuracy of about 20 ppm or less; such as a resolving power (FWHM) of 25,000 or better and accuracy of about 5 ppm or less; such as a resolving power (FWHM) of 25,000 or better and accuracy of about 3 ppm or less. Three exemplary mass spectrometers capable of exhibiting the requisite level of performance for glucagon ions are those which include orbitrap mass analyzers, certain TOF mass analyzers, or Fourier transform ion cyclotron resonance mass analyzers.

Elements found in biological active molecules, such as carbon, oxygen, and nitrogen, naturally exist in a number of different isotopic forms. For example, most carbon is present as $^{12}C$, but approximately 1% of all naturally occurring carbon is present as $^{13}C$. Thus, some fraction of naturally occurring carbon containing molecules will contain at least one $^{13}C$ atom. Inclusion of naturally occurring elemental isotopes in molecules gives rise to multiple molecular isotopic forms. The difference in masses of molecular isotopic forms is at least 1 atomic mass unit (amu). This is because elemental isotopes differ by at least one neutron (mass of one neutron≈1 amu). When molecular isotopic forms are ionized to multiply charged states, the mass distinction between the isotopic forms can become difficult to discern because mass spectrometric detection is based on the mass to charge ratio (m/z).

For example, two isotopic forms differing in mass by 1 amu that are both ionized to a 5+ state will exhibit differences in their m/z of only 0.2 (difference of 1 amu/charge state of 5). High resolution/high accuracy mass spectrometers are capable of discerning between isotopic forms of highly multiply charged ions (such as ions with charges of ±4, ±5, ±6, ±7, ±8, ±9, or higher).

Due to naturally occurring elemental isotopes, multiple isotopic forms typically exist for every molecular ion (each of which may give rise to a separately detectable spectrometric peak if analyzed with a sensitive enough mass spectrometric instrument). The m/z ratios and relative abundances of multiple isotopic forms collectively comprise an isotopic signature for a molecular ion. In some embodiments, the m/z and relative abundances of two or more molecular isotopic forms may be utilized to confirm the identity of a molecular ion under investigation. In some embodiments, the mass spectrometric peak from one or more isotopic forms is used to quantitate a molecular ion. In some related embodiments, a single mass spectrometric peak from one isotopic form is used to quantitate a molecular ion. In other related embodiments, a plurality of isotopic peaks are used to quantitate a molecular ion. In these later embodiments, the plurality of isotopic peaks may be subject to any appropriate mathematical treatment. Several mathematical treatments are known in the art and include, but are not limited to summing the area under multiple peaks or averaging the response from multiple peaks.

In mass spectrometry techniques generally, ions may be detected using several detection modes. For example, selected ions may be detected, i.e. using a selective ion monitoring mode (SIM), or alternatively, mass transitions resulting from collision activated dissociation (CAD), e.g., multiple reaction monitoring (MRM) or selected reaction monitoring (SRM). CAD is often used to generate fragment ions for further detection. In CAD, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy. Alternatively, neutral loss may be monitored.

In some embodiments, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

One may enhance the specificity of the MS technique by employing "tandem mass spectrometry," or "MS/MS". In this technique, a precursor ion (also called a parent ion) generated from a molecule of interest can be filtered in an MS instrument, and the precursor ion subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

Alternate modes of operating a tandem mass spectrometric instrument include product ion scanning and precursor ion scanning. For a description of these modes of operation, see, e.g., E. Michael Thurman, et al., Chromatographic-Mass Spectrometric Food Analysis for Trace Determination of Pesticide Residues, Chapter 8 (Amadeo R. Fernandez-Alba, ed., Elsevier 2005) (387).

The results of an analyte assay may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, external standards may be run with the samples, and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of glucagon. Methods of generating and using such standard curves are well known in the art and one of ordinary skill is capable of selecting an appropriate internal standard. For example, in preferred embodiments one or more forms of isotopically labeled glucagon may be used as internal standards. Numerous other methods for relating the amount of an ion to the amount of the original molecule will be well known to those of ordinary skill in the art.

As used herein, an "isotopic label" produces a mass shift in the labeled molecule relative to the unlabeled molecule when analyzed by mass spectrometric techniques. Examples of suitable labels include deuterium ($^2H$), $^{13}C$, and $^{15}N$. One or more isotopic labels can be incorporated at one or more positions in the molecule and one or more kinds of isotopic labels can be used on the same isotopically labeled molecule.

One or more steps of the methods may be performed using automated machines. In certain embodiments, one or more purification steps are performed on-line, and more preferably all of the purification and mass spectrometry steps may be performed in an on-line fashion.

In particularly preferred embodiments, glucagon in a sample is detected and/or quantified using MS/MS as follows. Samples are preferably subjected to SPE, then subjected to liquid chromatography, preferably HPLC; the flow of liquid solvent from a chromatographic column enters the heated nebulizer interface of an MS/MS analyzer; and the solvent/analyte mixture is converted to vapor in the heated charged tubing of the interface. During these processes, the analyte (i.e., glucagon) is analyzed. The ions, e.g. precursor ions, pass through the orifice of the instrument and enter the first quadrupole. Quadrupoles 1 and 3 (Q1 and Q3) are mass filters, allowing selection of ions (i.e., selection of "precursor" and "fragment" ions in Q1 and Q3, respectively) based on their mass to charge ratio (m/z). Quadrupole 2 (Q2) is the collision cell, where ions are fragmented. The first quadrupole of the mass spectrometer (Q1) selects for molecules with the mass to charge ratios of glucagon. Precursor ions with the correct mass/charge ratios are allowed to pass into the collision chamber (Q2), while unwanted ions with any other mass/charge ratio collide with the sides of the quadrupole and are eliminated. Precursor ions entering Q2 collide with neutral argon gas molecules and fragment. The fragment ions generated are passed into quadrupole 3 (Q3), where the fragment ions of glucagon are selected while other ions are eliminated.

The methods may involve MS/MS performed in either positive or negative ion mode; preferably positive ion mode. Using standard methods well known in the art, one of ordinary skill is capable of identifying one or more fragment ions of a particular precursor ion of glucagon that may be used for selection in quadrupole 3 (Q3).

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC-MS methods. The areas under the peaks corresponding to particular ions, or the amplitude of such peaks, may be measured and correlated to the amount of the analyte of interest. In certain embodiments, the area under the curves, or amplitude of the peaks, for fragment ion(s) and/or precursor ions are measured to determine the amount of glucagon. As described above, the relative abundance of a given ion may be converted into an absolute amount of the original analyte using calibration standard curves based on peaks of one or more ions of an internal or external molecular standard.

The following Examples serve to illustrate the invention. These Examples are in no way intended to limit the scope of the methods.

EXAMPLES

Example 1

Sample Preparation

Human patient serum samples were prepared for analysis as described in Example 2, below.

Mimic serum samples containing various amounts of glucagon were prepared by spiking synthetic glucagon in 40 mg/mL Bovine Serum Albumin (BSA) in Phosphate Buffered Saline (PBS) buffer. Glucagon standard was spiked in serially diluted human patient serum for assessment of linear response (discussed below in Example 5 and shown in FIG. 3).

Synthetic glucagon was also spiked in stripped sera (at concentrations of 0, 0.05, 0.1, 0.5, 1, 2, 5, 10, 20, and 50 ng/mL) and pooled patient sera (at concentrations of 0, 0.05, 0.1, 0.5, 1, 2, 5, and 10 ng/mL) to test LLOD and LLOQ for the methods described herein.

Example 2

Extraction of Glucagon from Samples Using Liquid Chromatography

Injection of 100 μL sample was performed with a Cohesive Technologies Aria TX-420 system using Aria OS V 1.6 or newer software.

100 μL samples were passed through a 0.2 μm micro-spin cellulose acetate delipidation filter to prevent particles and phospholipids from the samples prior to their introductions into a Water OASIS HLB 25 μm (2.1×20 mm), 85 A solid phase extraction (SPE) column. Alternatively, some samples were passed through a 0.45 μm micro-spin cellulose acetate delipidation filter prior to SPE. The solid phase extraction column retained glucagon while letting other serum proteins and large molecules flow through.

Glucagon was eluted off the extraction column and onto the analytical column (polar embedded C-8(2) analytical column from Phenomenex Inc. (5 μm particle size, 20×2.1 mm). An HPLC gradient was applied to the analytical column, to separate glucagon from other analytes contained in the sample. Mobile phase A was 0.2% formic acid in water and mobile phase B was 0.2% formic acid in acetonitrile. The HPLC gradient started with a 22% organic gradient which was ramped to 38% in approximately 120 seconds.

The separated samples are then ready for high resolution/high accuracy mass spectrometry (MS) or tandem mass spectrometry (MS/MS) as described in Examples 3 and 4, respectively.

Example 3

Detection of Glucagon by High Resolution/High Accuracy MS

High resolution/high accuracy MS was performed using a Thermo LTQ MS system (Thermo Electron Corporation). This system employed an ion trap MS analyzer capable of high resolution/high accuracy MS. The instrument exhibited resolution of approximately 25,000 FWHM, and mass accuracy of approximately 1 ppm while measuring glucagon.

Figure 1B:
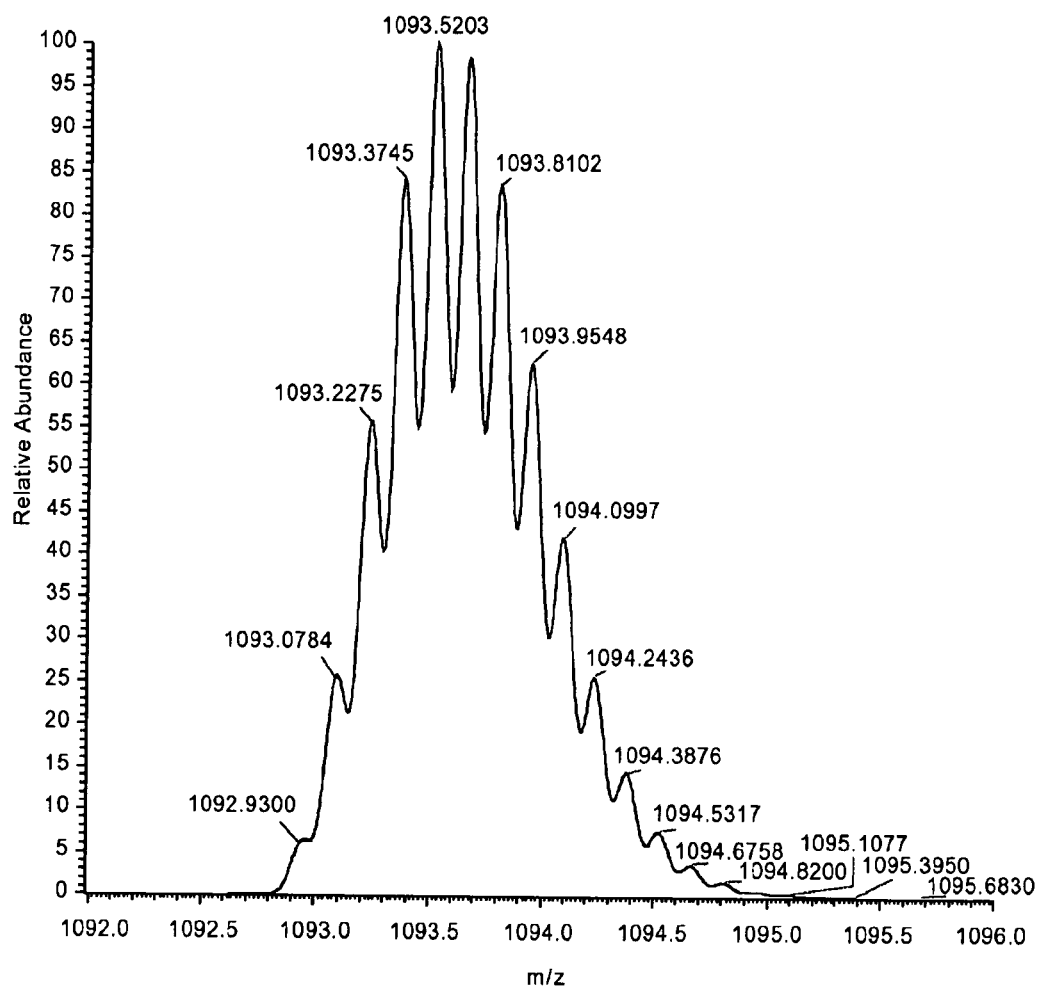
Figure 1C:
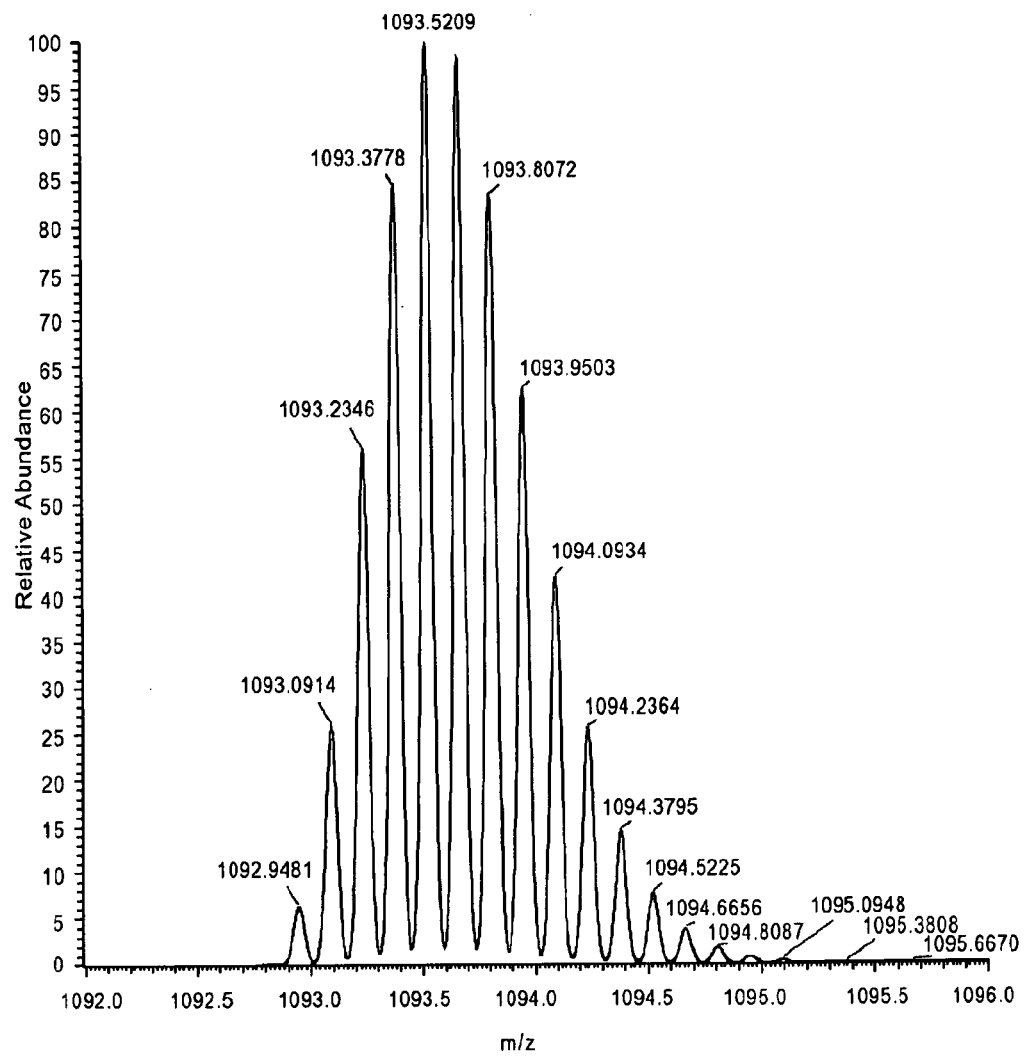

Ionization was conducted with an ESI source in positive ion mode. Multiply charged glucagon ions are observed with m/z of 871.1±0.50 (for the 4+ ion). Single MS spectra across the range of about 200 to 2000 m/z showing intact glucagon ions is seen in FIG. 1.

Figure 2A:
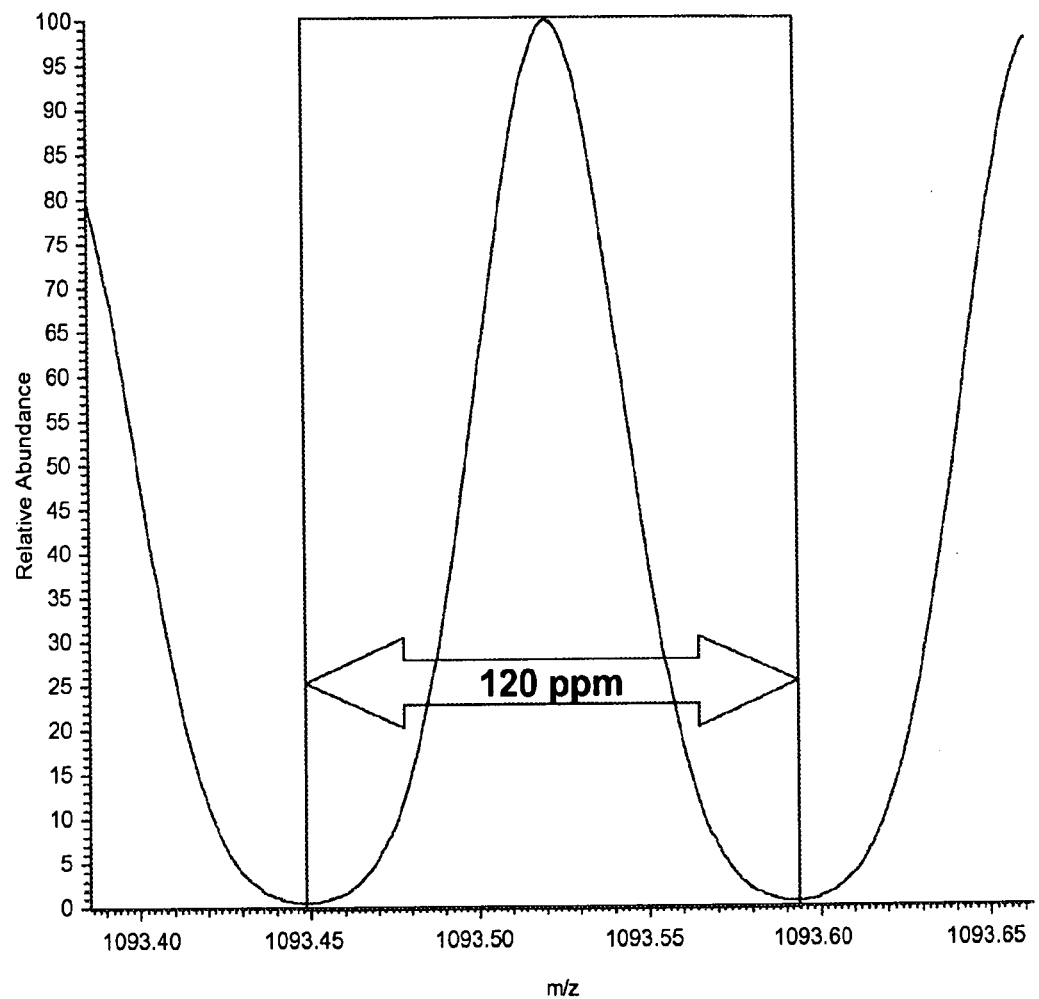
Figure 2B:
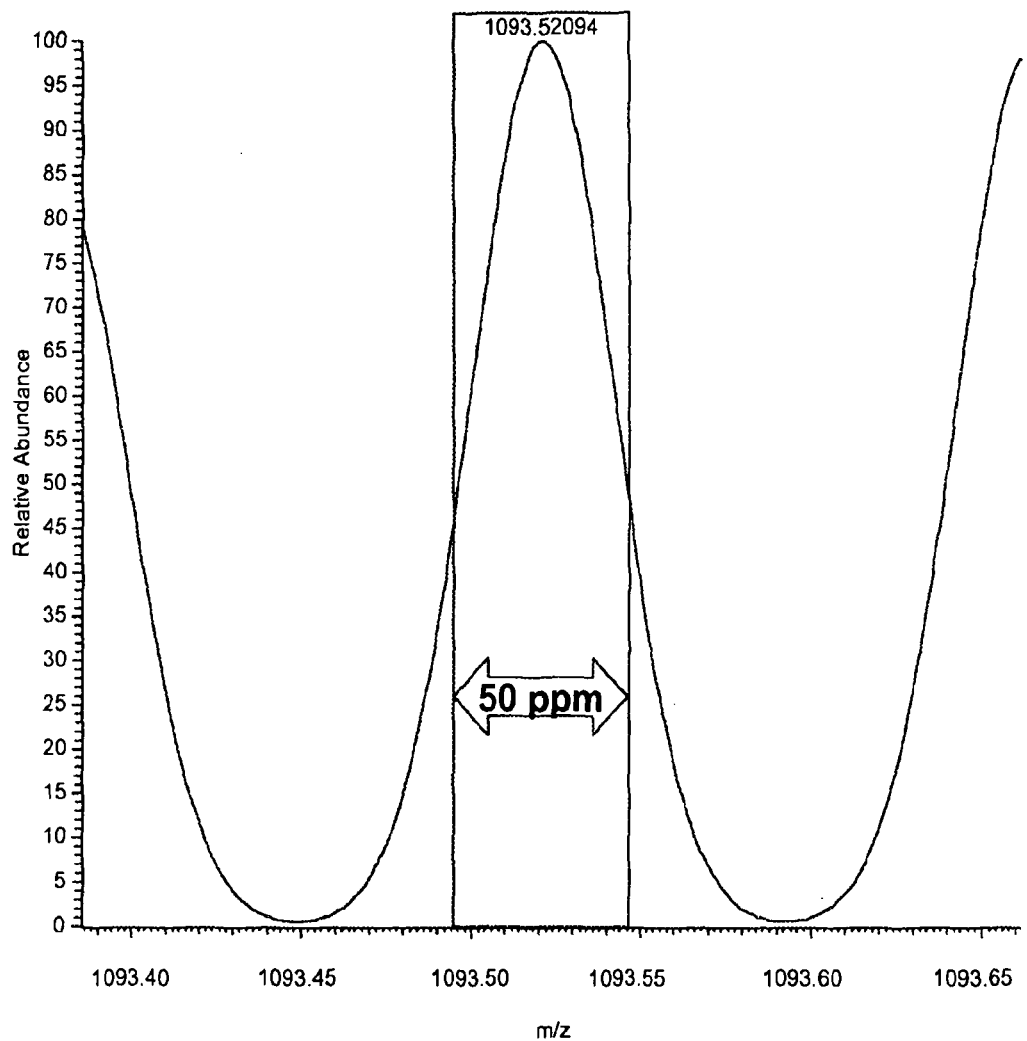
Figure 2D:
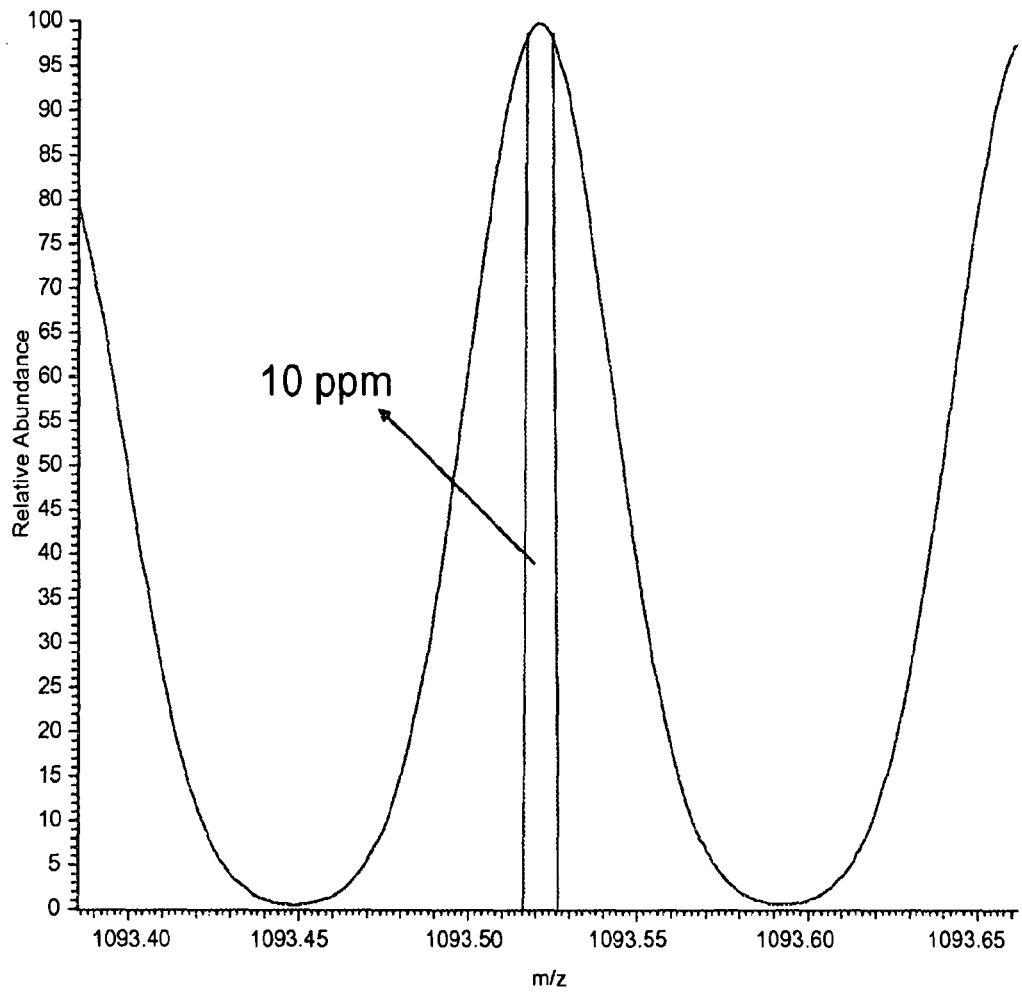

Fragmentation of the 4+ glucagon ions resulted in a plurality of fragment ions at various charge states. The fragment ions generated by fragmentation with the LTQ instrument include a fragment ion with a m/z of 1083.9±0.50 (3+ ion), 1040.2±0.50 (3+ ion), 841.8±0.50 (3+ ion), 940.8±0.50 (3+ ion), 1002.5±0.50 (3+ ion), 1122.2±0.50 (3+ ion), and 780.6±0.50 (4+ ion). An exemplary spectra showing fragment ions generated from glucagon precursor ions with a m/z of 871.1±0.50 on the LTQ instrument is demonstrated in FIG. 2.

Example 4

Detection and Quantitation of Glucagon by Tandem MS

MS/MS was performed using a Finnigan TSQ Quantum Ultra MS/MS system (Thermo Electron Corporation). The following software programs, all from Thermo Electron, were used in the Examples described herein: TSQ Ultra Quantum V 1.4.1 or newer, Xcalibur V 2.0 or newer, and LCQuan V 2.5 or newer. Liquid solvent/analyte exiting the analytical column flowed to the heated nebulizer interface of the MS/MS analyzer. The solvent/analyte mixture was converted to vapor in the heated tubing of the interface. Analytes were ionized by ESI.

Ions passed to the first quadrupole (Q1), which selected ions with a m/z of 871.1±0.50. Ions entering quadrupole 2 (Q2) collided with argon gas (at a collision cell energy of 28 V) to generate ion fragments, which were passed to quadrupole 3 (Q3) for further selection. Fragmentation spectra observed with a triple quadrupole tandem mass spectrometer by fragmentation of the 871.1±0.50 glucagon precursor ion was similar to that seen on the LTQ instrument (shown in FIG. 2). The following mass transitions were used for detection and quantitation during validation on positive polarity.

TABLE 1

Mass Transitions Observed for Glucagon (Positive Polarity)

| Analyte | Precursor Ion (m/z) | Product Ions (m/z) |
|---|---|---|
| Glucagon | 871.1 ± 0.50 | 780.6 ± 0.50n 841.8 ± 0.50, 940.8 ± 0.50, 1002.5 ± 0.50, 1040.2 ± 0.50, 1083.9 ± 0.50, and 1122.2 ± 0.50 |

Several of the observed product ions correspond with MS/MS ions indicated as possible by ProteinProspector 5.3.0, the results of which are shown in Table 2. The bolded entries have m/z ratios that correspond to those ions actually observed.

TABLE 2

Possible MS/MS Ions for Glucagon Based on Amino Acid Sequence

Possible Precursor Ions

| $MH^{+1}$ (av) | $MH^{+1}$ (mono) | $MH^{+2}$ (av) | $MH^{+2}$ (mono) | $MH^{+3}$ (av) | $MH^{+3}$ (mono) | $MH^{+4}$ (av) | $MH^{+4}$ (mono) |
|---|---|---|---|---|---|---|---|
| 3483.8 | 3481.6 | 1742.4 | 1741.3 | 1161.9 | 1161.2 | 871.7 | 871.1 |

Possible Fragment Ions

| m/z | Ion |
|---|---|
| $113.1^{+2}$ | $b_2^{+2}$ |
| 120.1 | $y_1$ |
| $177.2^{+2}$ | $b_3^{+2}$ |
| $205.7^{+2}$ | $b_4^{+2}$ |
| 225.2 | $b_2$ |
| 234.2 | $y_2$ |
| $256.3^{+2}$ | $b_5^{+2}$ |
| $329.9^{+2}$ | $b_6^{+2}$ |
| 353.4 | $b_3$ |
| 365.4 | $y_3$ |
| $380.4^{+2}$ | $b_7^{+2}$ |
| 410.4 | $b_4$ |
| $423.9^{+2}$ | $b_8^{+2}$ |
| $447.5^{+3}$ | $b_{12}^{+3}$ |
| 478.6 | $y_4$ |
| $481.5^{+2}$ | $b_9^{+2}$ |
| $494.5^{+4}$ | $b_{17}^{+4}$ |
| $501.9^{+3}$ | $b_{13}^{+3}$ |
| 511.5 | $b_5$ |
| $533.6^{+4}$ | $b_{18}^{+4}$ |
| $539.6^{+3}$ | $b_{14}^{+3}$ |
| $551.3^{+4}$ | $b_{19}^{+4}$ |
| $556.0^{+3}$ | $y_{13}^{+3}$ |
| $563.1^{+2}$ | $b_{10}^{+2}$ |
| $568.9^{+4}$ | $y_{18}^{+4}$ |
| $577.9^{+3}$ | $b_{15}^{+3}$ |
| $583.4^{+4}$ | $b_{20}^{+4}$ |
| $585.0^{+3}$ | $y_{14}^{+3}$ |
| $590.7^{+4}$ | $y_{19}^{+4}$ |
| $606.6^{+2}$ | $b_{11}^{+2}$ |
| $607.0^{+3}$ | $b_{16}^{+3}$ |
| $612.2^{+4}$ | $b_{21}^{+4}$ |
| $623.4^{+3}$ | $Y_{15}^{+3}$ |
| $631.5^{+4}$ | $Y_{20}^{+4}$ |
| $648.9^{+4}$ | $B_{22}^{+4}$ |
| 658.7 | $b_6$ |
| $659.0^{+3}$ | $B_{17}^{+3}$ |
| $660.2^{+4}$ | $Y_{21}^{+4}$ |
| $661.1^{+3}$ | $Y_{16}^{+3}$ |
| 664.8 | $y_5$ |
| $670.7^{+2}$ | $B_{12}^{+2}$ |
| $673.7^{+4}$ | $B_{23}^{+4}$ |
| $682.0^{+4}$ | $Y_{22}^{+4}$ |
| $705.8^{+4}$ | $B_{24}^{+4}$ |
| $707.3^{+4}$ | $Y_{23}^{+4}$ |
| $711.1^{+3}$ | $B_{18}^{+3}$ |
| $715.5^{+3}$ | $Y_{17}^{+3}$ |
| $734.8^{+3}$ | $B_{19}^{+3}$ |

TABLE 2-continued

Possible MS/MS Ions for Glucagon Based on Amino Acid Sequence

| m/z | Ion |
|---|---|
| $744.1^{+4}$ | $Y_{24}^{+4}$ |
| $752.3^{+2}$ | $B_{13}^{+2}$ |
| $752.3^{+4}$ | $B_{25}^{+4}$ |
| $755.4^{+2}$ | $Y_{12}^{+2}$ |
| $758.2^{+3}$ | $Y_{18}^{+3}$ |
| 759.8 | $b_7$ |
| $769.4^{+4}$ | $Y_{25}^{+4}$ |
| $777.5^{+3}$ | $B_{20}^{+3}$ |
| $780.6^{+4}$ | $B_{26}^{+4}$ |
| $783.6^{+4}$ | $Y_{26}^{+4}$ |
| $787.2^{+3}$ | $Y_{19}^{+3}$ |
| 792.9 | $y_6$ |
| $808.9^{+2}$ | $B_{14}^{+2}$ |
| $813.4^{+4}$ | $B_{27}^{+4}$ |
| $815.7^{+4}$ | $Y_{27}^{+4}$ |
| $815.9^{+3}$ | $B_{21}^{+3}$ |
| $833.5^{+2}$ | $y_{13}^{+2}$ |
| $837.4^{+4}$ | $y_{28}^{+4}$ |
| $841.6^{+3}$ | $y_{20}^{+3}$ |
| $841.9^{+4}$ | $b_{28}^{+4}$ |
| 846.9 | $b_8$ |
| $864.9^{+3}$ | $b_{22}^{+3}$ |
| $866.4^{+2}$ | $b_{15}^{+2}$ |
| $871.7^{+4}$ | $MH^{+4}$ |
| $877.0^{+2}$ | $y_{14}^{+2}$ |
| $880.0^{+3}$ | $y_{21}^{+3}$ |
| 892.1 | $y_7$ |
| $898.0^{+3}$ | $b_{23}^{+3}$ |
| $909.0^{+3}$ | $y_{22}^{+3}$ |
| $910.0^{+2}$ | $b_{16}^{+2}$ |
| $934.6^{+2}$ | $y_{15}^{+2}$ |
| $940.7^{+3}$ | $b_{24}^{+3}$ |
| $942.7^{+3}$ | $y_{23}^{+3}$ |
| 962.0 | $b_9$ |
| $988.0^{+2}$ | $b_{17}^{+2}$ |
| $991.1^{+2}$ | $y_{16}^{+2}$ |
| $991.8^{+3}$ | $y_{24}^{+3}$ |
| $1002.8^{+3}$ | $b_{25}^{+3}$ |
| $1025.5^{+3}$ | $y_{25}^{+3}$ |
| 1039.2 | $y_8$ |
| $1040.5^{+3}$ | $b_{26}^{+3}$ |
| $1044.5^{+3}$ | $y_{26}^{+3}$ |
| $1066.1^{+2}$ | $b_{18}^{+2}$ |
| $1072.7^{+2}$ | $y_{17}^{+2}$ |
| $1084.2^{+3}$ | $b_{27}^{+3}$ |
| $1087.2^{+3}$ | $y_{27}^{+3}$ |
| $1101.7^{+2}$ | $b_{19}^{+2}$ |
| $1116.23^{+3}$ | $y_{28}^{+3}$ |
| $1122.23^{+3}$ | $b_{28}^{+3}$ |
| 1125.1 | $b_{10}$ |
| $1136.8^{+2}$ | $y_{18}^{+2}$ |
| 1154.3 | $y_9$ |
| $1161.9^{+3}$ | $MH^{+3}$ |
| $1165.8^{+2}$ | $b_{20}^{+2}$ |
| $1180.3^{+2}$ | $y_{19}^{+2}$ |
| 1212.2 | $b_{11}$ |
| $1223.3^{+2}$ | $b_{21}^{+2}$ |
| $1261.9^{+2}$ | $y_{20}^{+2}$ |
| 1282.5 | $y_{10}$ |
| $1296.9^{+2}$ | $b_{22}^{+2}$ |
| $1319.5^{+2}$ | $y_{21}^{+2}$ |
| 1340.4 | $b_{12}$ |
| $1346.5^{+2}$ | $b_{23}^{+2}$ |
| 1353.5 | $y_{11}$ |
| $1363.0^{+2}$ | $y_{22}^{+2}$ |
| $1410.5^{+2}$ | $b_{24}^{+2}$ |
| $1413.6^{+2}$ | $y_{23}^{+2}$ |
| $1487.2^{+2}$ | $y_{24}^{+2}$ |
| 1503.6 | $b_{13}$ |
| $1503.6^{+2}$ | $b_{25}^{+2}$ |
| 1509.7 | $y_{12}$ |
| $1537.7^{+2}$ | $y_{25}^{+2}$ |
| $1560.2^{+2}$ | $b_{26}^{+2}$ |
| $1566.2^{+2}$ | $y_{26}^{+2}$ |
| 1616.7 | $b_{14}$ |
| $1625.8^{+2}$ | $b_{27}^{+2}$ |
| $1630.3^{+2}$ | $y_{27}^{+2}$ |

TABLE 2-continued

Possible MS/MS Ions for Glucagon Based on Amino Acid Sequence

| | |
|---|---|
| 1665.9 | $y_{13}$ |
| 1673.8$^{+2}$ | $y_{28}^{+2}$ |
| 1682.9$^{+2}$ | $b_{28}^{+2}$ |
| 1731.8 | $b_{15}$ |
| 1742.4$^{+2}$ | $MH^{+2}$ |
| 1753.0 | $y_{14}$ |
| 1818.9 | $b_{16}$ |
| 1868.1 | $y_{15}$ |
| 1975.1 | $b_{17}$ |
| 1981.3 | $y_{16}$ |
| 2131.3 | $b_{18}$ |
| 2144.4 | $y_{17}$ |
| 2202.4 | $b_{19}$ |
| 2272.6 | $y_{18}$ |
| 2330.5 | $b_{20}$ |
| 2359.7 | $y_{19}$ |
| 2445.6 | $b_{21}$ |
| 2522.9 | $y_{20}$ |
| 2592.8 | $b_{22}$ |
| 2638.0 | $y_{21}$ |
| 2691.9 | $b_{23}$ |
| 2725.0 | $y_{22}$ |
| 2820.0 | $b_{24}$ |
| 2826.1 | $y_{23}$ |
| 2973.3 | $y_{24}$ |
| 3006.2 | $b_{25}$ |
| 3074.4 | $y_{25}$ |
| 3119.4 | $b_{26}$ |
| 3131.5 | $y_{26}$ |
| 3250.6 | $b_{27}$ |
| 3259.6 | $y_{27}$ |
| 3346.7 | $y_{28}$ |
| 3364.7 | $b_{28}$ |
| 3483.8 | MH |

Of the observed transitions, two were monitored in MRM mode for quantitative analysis: fragmentation of the precursor ion with m/z of 871.1±0.50 to fragment ions with m/z of 1083.9±0.50 and 1040.2±0.50. Additional fragment ions may be selected to replace or augment either of the selected fragment ions.

Example 5

Data Analysis for Quantitation of Glucagon

Glucagon quantitation via monitoring the indicated transitions with a triple quadrupole tandem mass spectrometer was conducted on glucagon spiked mimic serum samples, stripped serum samples, and pooled patient serum samples.

Figure 3:
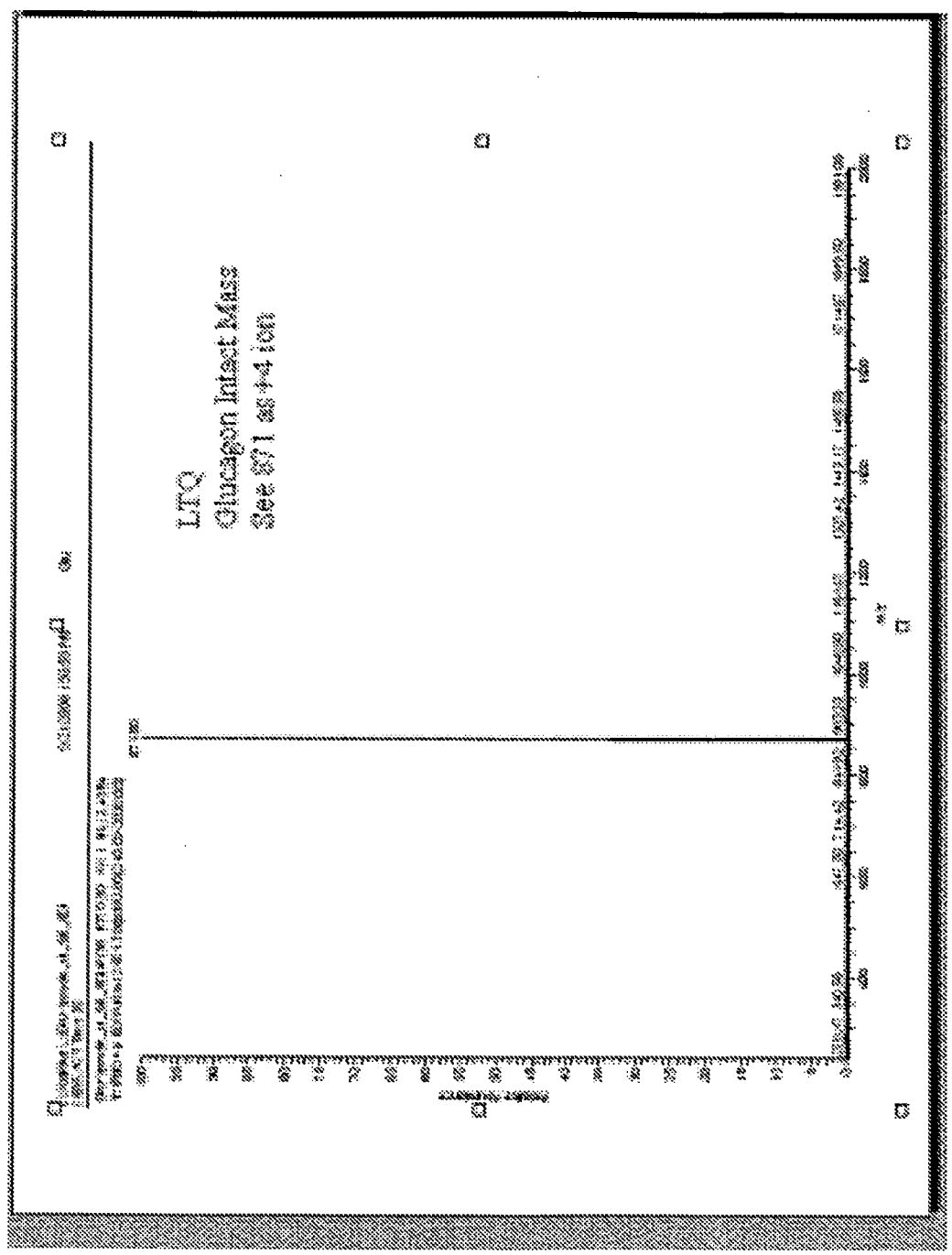
FIG. 3 shows an exemplary single MS spectra across the range of about 200 to 2000 m/z for glucagon as collected by a high resolution/high accuracy linear ion trap mass spectrometric instrument. Details are discussed in Example 3.
Figure 4:
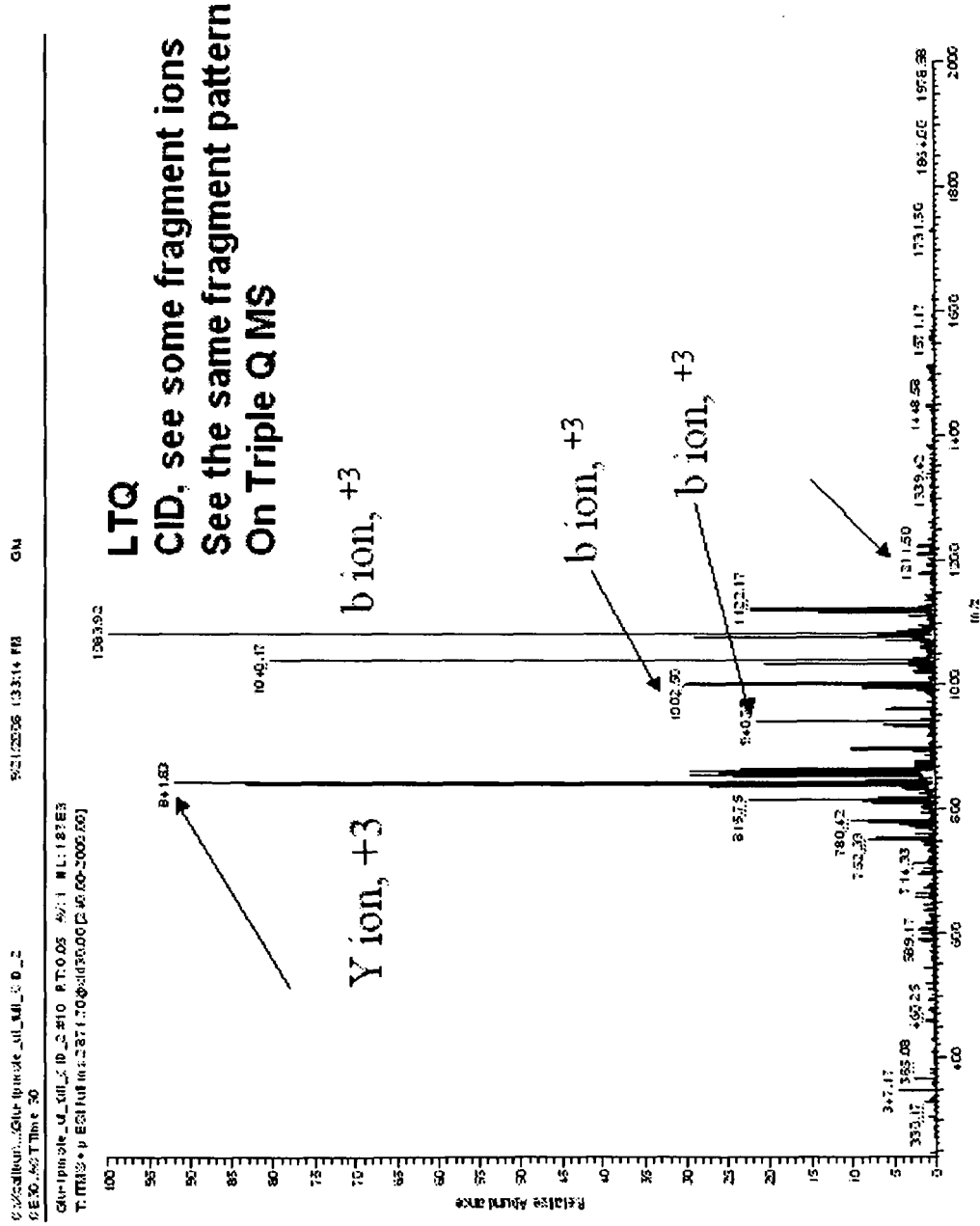
FIG. 4 shows a plot of an exemplary fragmentation spectra generated from fragmenting glucagon precursor ions with a m/z of 871.1±0.50 on a high resolution/high accuracy linear ion trap mass spectrometric instrument. Details are discussed in Example 3.
Figure 5:
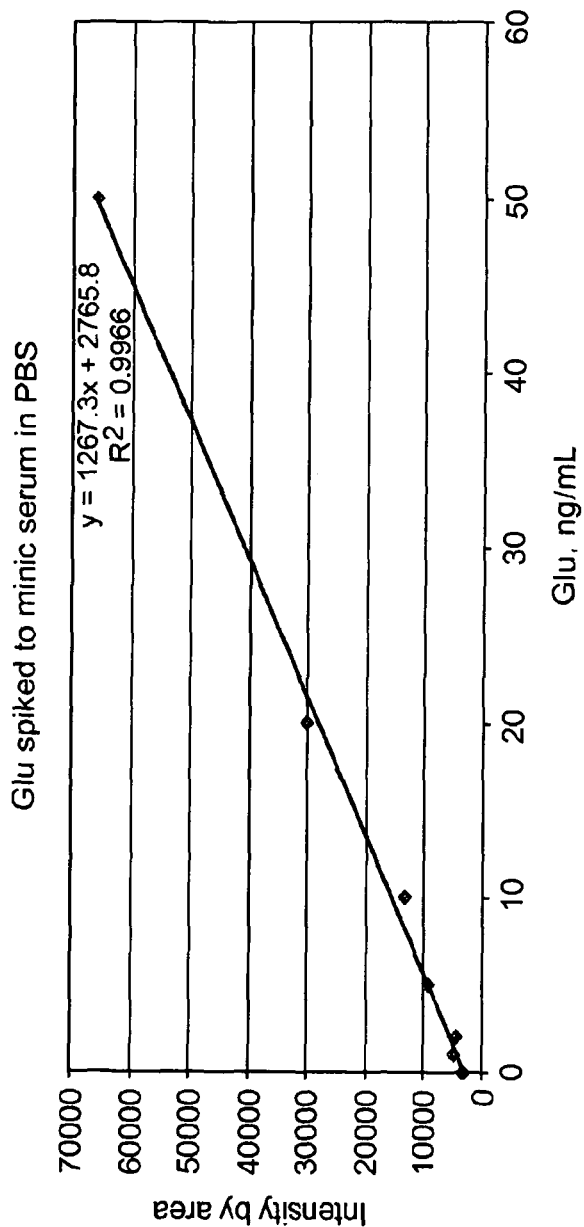
FIG. 5 shows a plot of the linearity of quantitation of glucagon in spiked mimic serum standards. Details are described in Example 4.

To establish the linearity of glucagon detection in the assay, several spiked mimic serum standards, spiked stripped serum samples, and spiked pooled patient sera samples were analyzed across a concentration range of 0 ng/mL to about 50 ng/mL. Graphs showing the linearity of the data for glucagon detection in spiked mimic serum standards, spiked stripped serum samples, and spiked pooled patient sera samples are shown in FIGS. 3-5, respectively.

Figure 6:
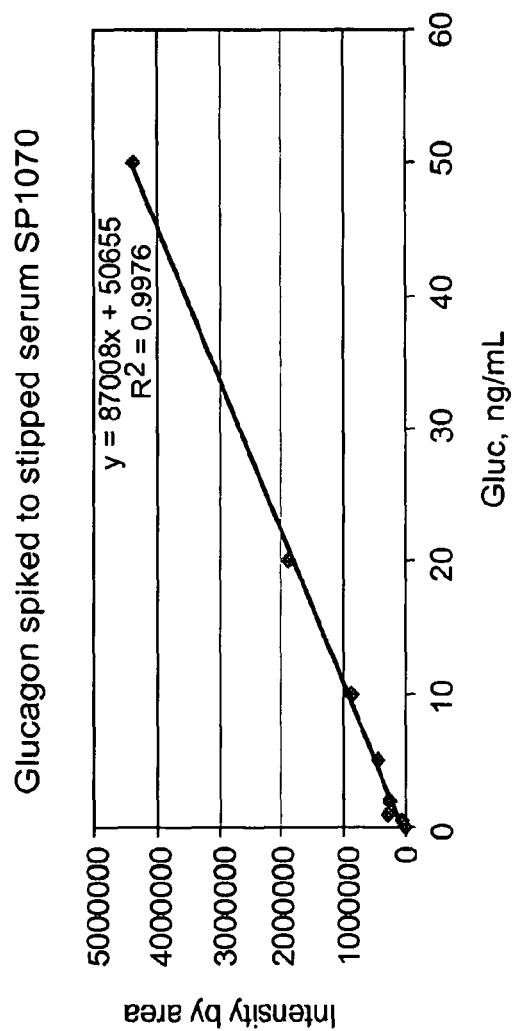
FIG. 6 shows a plot of the linearity of quantitation of glucagon in spiked stripped serum samples. Details are described in Example 4.
Figure 7:
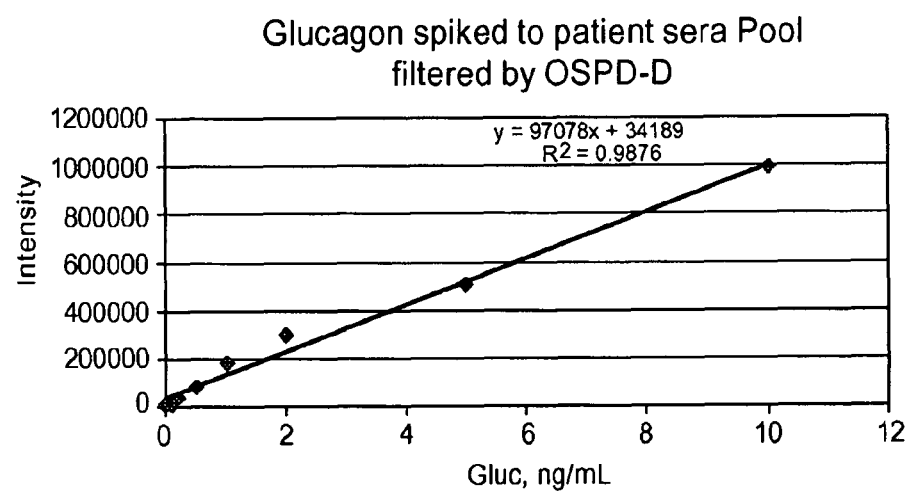
FIG. 7 shows a plot of the linearity of quantitation of glucagon in spiked pooled patient sera samples. Details are described in Example 4.
Figure 8:
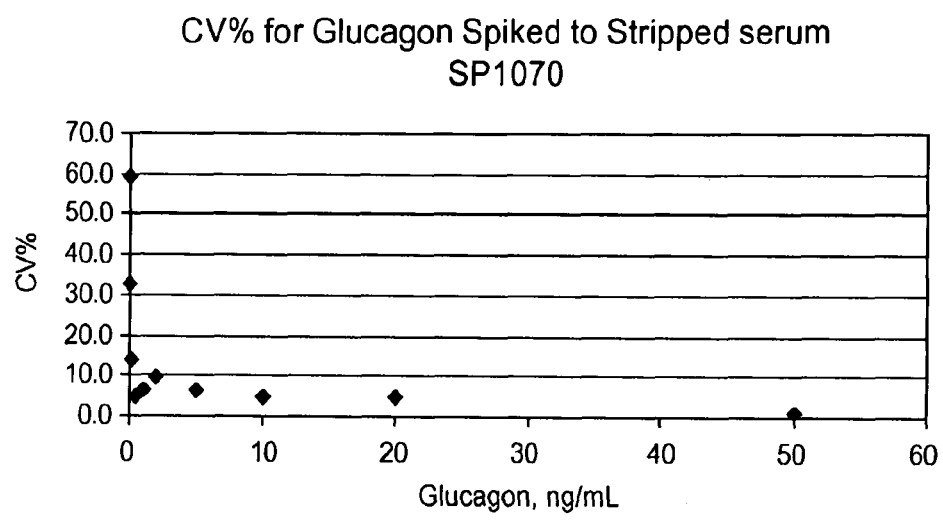
FIG. 8 shows a plot of exemplary data used to assess LLOQ of glucagon in spiked stripped serum samples.
Figure 9:
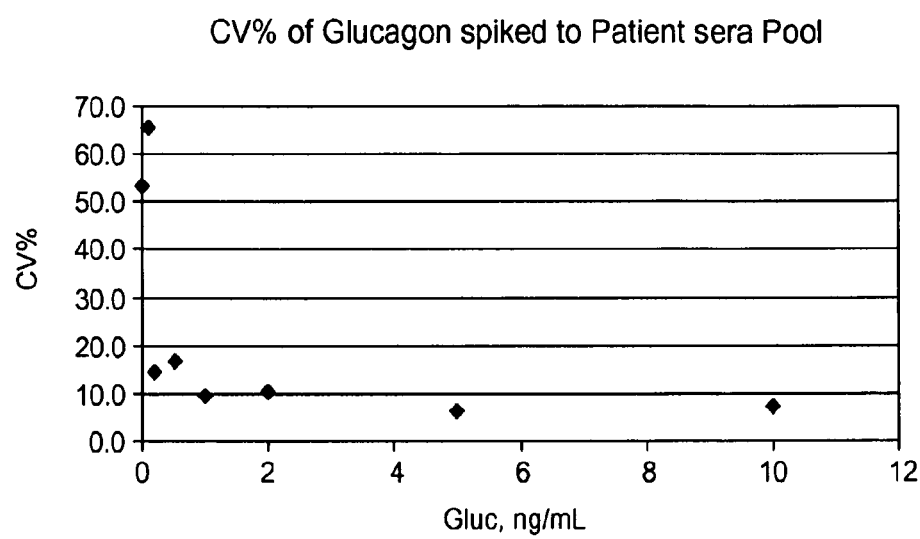
FIG. 9 shows a plot of exemplary data used to assess LLOQ of glucagon in pooled patient sera samples.

The LLOQ is the point where measurements become quantitatively meaningful. The analyte response at this LLOQ is identifiable, discrete and reproducible with a precision of greater than 20%. The LLOQ was determined by assaying duplicates of spiked stripped sera samples and duplicates of spiked pooled patient sera samples, then determining the reproducibility. Analysis of the collected data indicates that samples with concentrations of greater than about 100 pg/mL or above had CVs less than 20%. Representative data from several analyses are shown in Table 3. Thus, the LLOQ of this assay was determined to be about 200 pg/mL. The collected data is shown plotted in FIGS. 6 and 7 for the stripped sera and pooled patient sera samples, respectively.

TABLE 3

Spiked Glucagon Concentration and Observed Coefficient of Variations

| Glucagon Concentration (ng/mL) (Stripped Sera Samples) | CV (%) | Glucagon Concentration (ng/mL) (Pooled Patient Sera Samples) | CV (%) |
|---|---|---|---|
| 0 | 59.0 | 0 | 53.3 |
| 0.05 | 32.8 | 0.05 | 65.4 |
| 0.1 | 13.8 | 0.1 | 14.5 |
| 0.5 | 5 | 0.5 | 16.8 |
| 1 | 6.5 | 1 | 9.3 |
| 2 | 9.9 | 2 | 10.3 |
| 5 | 6.4 | 5 | 6.4 |
| 10 | 5.0 | 10 | 7.2 |
| 20 | 4.6 | — | — |
| 50 | 1.2 | — | — |

The LOD is the point at which a value is beyond the uncertainty associated with its measurement and is defined as three standard deviations from the zero concentration. To determine the LOD for the glucagon assay, replicates of spiked stripped serum were assayed, and the results analyzed. The LOD for this assay was 100 pg/mL in spiked stripped serum.

Example 6

Enrichment of Glucagon with Anti-Glucagon Antibody

Immunopurification methods may be used in addition to or instead of any of the purification steps described in Example 2. When using immunopurification methods, initial patient sample volumes of between about 200 to 500 μL are enriched by capture and extraction of glucagon with anti-glucagon antibodies prior to SPE or HPLC.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. A method for determining the amount of glucagon in a sample by tandem mass spectrometry, said method comprising:
   a. subjecting the sample to ionization under conditions suitable to produce one or more ions detectable by mass spectrometry, wherein said ions comprise a glucagon precursor ion with a mass to charge ratio (m/z) of 871.1±0.50;
   b. fragmenting a glucagon precursor ion with a mass to charge ratio (m/z) of 871.1±0.50 to produce one or more fragment ions, wherein one or more of said fragment ions are selected from the group consisting of ions with m/z of 780.6±0.50, 841.8±0.50, 940.8±0.50, 1002.5±0.50, 1040.2±0.50, 1083.9±0.50, and 1122.2±0.50;
   c. determining the amount of one or more ions produced in steps a and b; and
   d. using the amount of the one or more ions determined in step c to determine the amount of glucagon in the sample.

2. The method of claim 1, wherein one or more of said fragment ions are selected from the group consisting of ions with m/z of 1040.2±0.50 and 1083.9±0.50.

3. The method of claim 1, wherein ionization is conducted with an electrospray ionization (ESI) source.

4. The method of claim 1, wherein the sample is subjected to solid phase extraction (SPE) prior to ionization.

5. The method of claim 4, wherein said SPE and tandem mass spectrometry are conducted with on-line processing.

6. The method of claim 1, wherein the sample is subjected to high performance liquid chromatography (HPLC) prior to ionization.

7. The method of claim 1, wherein the sample is subjected to immunopurification prior to ionization.

8. The method of claim 7, wherein the immunopurification comprises capture and extraction of glucagon in said sample with anti-glucagon antibodies.

9. The method of claim 1, wherein the sample comprises plasma or serum.

10. The method of claim 1, wherein the method is capable of detecting glucagon at levels within the range of 60 pg/mL to 500 pg/mL, inclusive.

11. A method for determining the amount of glucagon in a sample by mass spectrometry, said method comprising:
   a. subjecting the sample to ionization under conditions suitable to produce one or more ions detectable by mass spectrometry;
   b. determining the amount of said one or more ions by tandem mass spectrometry; and
   c. using the amount of the one or more ions determined in step b to determine the amount of glucagon in the sample;
   wherein the method is capable of detecting glucagon at levels within the range of 60 pg/mL to 500 pg/mL, inclusive.

12. The method of claim 11, wherein ionization is conducted with an electrospray ionization (ESI) source.

13. The method of claim 11, wherein the method is capable of detecting glucagon at levels within the range of 60 pg/mL to 250 pg/mL, inclusive.

14. The method of claim 11, wherein the sample is subjected to solid phase extraction (SPE) prior to ionization.

15. The method of claim 14, wherein said SPE and tandem mass spectrometry are conducted with on-line processing.

16. The method of claim 11, wherein the sample is subjected to high performance liquid chromatography (HPLC) prior to ionization.

17. The method of claim 11, wherein the sample is subjected to immunopurification prior to ionization.

18. The method of claim 17, wherein the immunopurification comprises capture and extraction of glucagon in said sample with anti-glucagon antibodies.

19. The method of claim 11, wherein the sample comprises plasma or serum.

20. The method of claim 11, wherein tandem mass spectrometry comprises fragmenting a precursor ion with a mass to charge ratio (m/z) of 871.1±0.50 into one or more fragment ions.

21. The method of claim 20, wherein said fragment ions comprise one or more ions selected from the group consisting of ions with m/z of 780.6±0.50, 841.8±0.50, 940.8±0.50, 1002.5±0.50, 1040.2±0.50, 1083.9±0.50, and 1122.2±0.50.

22. The method of claim 20, wherein said fragment ions comprise one or more ions selected from the group consisting of ions with m/z of 1040.2±0.50 and 1083.9±0.50.

23. A method for determining the amount of glucagon in a sample by high resolution/high accuracy mass spectrometry, said method comprising:
   a. subjecting the sample to ionization under conditions suitable to produce one or more ions detectable by mass spectrometry;
   b. determining the amount of said one or more ions by high resolution/high accuracy mass spectrometry; and
   c. using the amount of the one or more ions determined in step b to determine the amount of glucagon in the sample;
   wherein said high resolution/high accuracy mass spectrometry is conducted with a mass analyzer capable of a FWHM of greater than or equal to about 10,000 and an accuracy of less than or equal to about 50 ppm.

24. The method of claim 23, wherein one or more of said determined ions are selected from the group consisting of ions with mass to charge ratios of 780.6±0.50, 841.8±0.50, 871.1±0.50, 940.8±0.50, 1002.5±0.50, 1040.2±0.50, 1083.9±0.50, and 1122.2±0.50.

25. The method of claim 23, wherein said high resolution/high accuracy mass spectrometry is conducted with an orbitrap mass spectrometer.

26. The method of claim 23, wherein the high resolution/high accuracy mass spectrometry is conducted with a time of flight (TOF) mass spectrometer.

27. The method of claim 23, wherein said high resolution/high accuracy mass spectrometry is conducted with an orbitrap or time of flight mass analyzer capable of a FWHM of greater than or equal to about 20,000 and an accuracy of less than or equal to about 10 ppm.

28. The method of claim 23, wherein said step of determining the amount of one or more ions comprises collecting spectrometric data from one or more peaks with each peak resulting from an isotopic form of said one or more ions.

29. The method of claim 28, wherein two or more peaks each resulting from a different isotopic form of an ion are used to confirm the identity of a glucagon ion or spectrometric data from two or more peaks each resulting from a single isotopic form of an ion are used to determine the amount of glucagon in said sample.

30. The method of claim 28, wherein spectrometric data from a peak resulting from a single isotopic form of an ion is used to determine the amount of glucagon in said sample.

* * * * *